(12) United States Patent
Belson et al.

(10) Patent No.: US 10,149,677 B2
(45) Date of Patent: Dec. 11, 2018

(54) VESSEL ACCESS AND CLOSURE DEVICE

(71) Applicant: VasoStitch, Inc., Menlo Park, CA (US)

(72) Inventors: Amir Belson, Los Altos, CA (US); Joelle Faulkner, London (CA); Phillip Charles Burke, Pala, CA (US); Eric T. Johnson, Temecula, CA (US); Bauback Safa, San Francisco, CA (US)

(73) Assignee: VasoStitch, Inc., Santa Cruz, CA (US)

(*) Notice: Subject to any disclaimer, the term of this patent is extended or adjusted under 35 U.S.C. 154(b) by 437 days.

(21) Appl. No.: 14/732,719

(22) Filed: Jun. 6, 2015

(65) Prior Publication Data

US 2015/0265272 A1    Sep. 24, 2015

Related U.S. Application Data

(60) Division of application No. 13/224,666, filed on Sep. 2, 2011, now Pat. No. 9,078,633, which is a
(Continued)

(51) Int. Cl.
*A61B 17/04* (2006.01)
*A61B 17/00* (2006.01)
*A61B 17/06* (2006.01)

(52) U.S. Cl.
CPC ...... *A61B 17/0469* (2013.01); *A61B 17/0057* (2013.01); *A61B 17/0482* (2013.01);
(Continued)

(58) Field of Classification Search
CPC ............ A61B 17/0469; A61B 17/0057; A61B 17/00482; A61B 2017/06076; A61B 2017/06171
See application file for complete search history.

(56) References Cited

U.S. PATENT DOCUMENTS 4,204,541 A   5/1980  Kapitanov
4,641,652 A   2/1987  Hutterer et al.
(Continued)

FOREIGN PATENT DOCUMENTS

CN         1886096 A      12/2006
DE    202010000329 U1      5/2010
(Continued)

OTHER PUBLICATIONS

International search report and written opinion dated Nov. 4, 2015 for PCT Application No. US2015/043312.
(Continued)

*Primary Examiner* — Katherine Rodjom
(74) *Attorney, Agent, or Firm* — Wilson Sonsini Goodrich & Rosati

(57) ABSTRACT

A vessel access and closure device places a running suture in the wall of a blood vessel using a rotating helical suture needle that carries the suture along a helical path passing through the vessel wall, then reverses rotation to release a suture anchor attached to the distal end of the suture. A loose helical coil of suture is left behind as the helical suture needle withdraws. The device is withdrawn and replaced with a vessel dilator and an introducer sheath that opens up a larger access opening into the blood vessel and creates a pathway that passes though the helical coil of suture for introducing an interventional device into the blood vessel. After the interventional procedure is completed, the interventional device and the introducer sheath are withdrawn and the running suture is tightened and secured with a suture lock to close the access opening into the vessel.

41 Claims, 25 Drawing Sheets

Related U.S. Application Data continuation of application No. PCT/US2010/027321, filed on Mar. 15, 2010.

(60) Provisional application No. 61/210,018, filed on Mar. 14, 2009.

(52) U.S. Cl.
CPC ............... *A61B 2017/00663* (2013.01); *A61B 2017/00778* (2013.01); *A61B 2017/06076* (2013.01)

(56) References Cited

U.S. PATENT DOCUMENTS

| | | |
|---|---|---|
| 4,964,468 A | 10/1990 | Adams et al. |
| 5,356,424 A | 10/1994 | Buzerak et al. |
| 5,407,527 A | 4/1995 | Ferrante et al. |
| 5,527,342 A | 6/1996 | William et al. |
| 5,545,148 A | 8/1996 | Wurster |
| 5,562,685 A | 10/1996 | Mollenauer et al. |
| 5,577,993 A | 11/1996 | Zhu et al. |
| 5,626,613 A | 5/1997 | Schmieding |
| 5,782,844 A | 7/1998 | Yoon et al. |
| 5,820,631 A | 10/1998 | Nobles |
| 5,931,855 A | 8/1999 | Buncke |
| 5,947,983 A | 9/1999 | Solar et al. |
| 6,287,250 B1 | 9/2001 | Peng et al. |
| 6,626,917 B1 | 9/2003 | Craig |
| 7,637,918 B2 | 12/2009 | Dant |
| 7,758,595 B2 | 7/2010 | Allen et al. |
| 7,780,701 B1 | 8/2010 | Meridew et al. |
| 8,500,757 B2 | 8/2013 | Miraki et al. |
| 9,078,633 B2 | 7/2015 | Belson et al. |
| 9,277,915 B2 | 3/2016 | Belson et al. |
| 2003/0074023 A1 | 4/2003 | Kaplan et al. |
| 2004/0002735 A1 | 1/2004 | Lizardi et al. |
| 2004/0060410 A1 | 4/2004 | Leung et al. |
| 2004/0138706 A1 | 7/2004 | Abrams et al. |
| 2004/0147957 A1 | 7/2004 | Pierson |
| 2005/0021057 A1 | 1/2005 | St. Goar et al. |
| 2005/0070959 A1 | 3/2005 | Cichocki et al. |
| 2005/0165414 A1 | 7/2005 | Craig et al. |
| 2005/0267520 A1 | 12/2005 | Modesitt |
| 2006/0036265 A1 | 2/2006 | Dant |
| 2006/0074484 A1 | 4/2006 | Huber et al. |
| 2006/0212048 A1 | 9/2006 | Crainich |
| 2006/0253127 A1 | 11/2006 | Bjerken |
| 2007/0005109 A1 | 1/2007 | Popadiuk et al. |
| 2007/0027454 A1 | 2/2007 | Modesitt et al. |
| 2007/0112422 A1 | 5/2007 | Dehdashtian et al. |
| 2008/0109036 A1 | 5/2008 | Stopek et al. |
| 2008/0234731 A1 | 9/2008 | Leung et al. |
| 2008/0275473 A1 | 11/2008 | Filipi et al. |
| 2008/0306333 A1 | 12/2008 | Chin |
| 2009/0054926 A1 | 2/2009 | Pipenhagen et al. |
| 2009/0082788 A1 | 3/2009 | Elmaraghy |
| 2009/0187116 A1 | 7/2009 | Noishiki et al. |
| 2009/0240264 A1 | 9/2009 | Tuval et al. |
| 2009/0275960 A1 | 11/2009 | Provenza et al. |
| 2009/0287183 A1 | 11/2009 | Bishop et al. |
| 2010/0063542 A1 | 3/2010 | Van et al. |
| 2010/0087855 A1 | 4/2010 | Leung et al. |
| 2010/0114306 A1 | 5/2010 | Lenihan et al. |
| 2010/0268253 A1 | 10/2010 | Ahlberg et al. |
| 2010/0274129 A1 | 10/2010 | Hooven |
| 2011/0004235 A1 | 1/2011 | Sundt, III et al. |
| 2011/0015728 A1 | 1/2011 | Jimenez et al. |
| 2011/0190811 A1 | 8/2011 | Shanley |
| 2011/0238090 A1 | 9/2011 | Heneveld |
| 2012/0035654 A1 | 2/2012 | Amir |
| 2012/0065677 A1 | 3/2012 | West, Jr. |
| 2012/0089181 A1 | 4/2012 | Shanley et al. |
| 2012/0116418 A1 | 5/2012 | Amir et al. |
| 2015/0073478 A1 | 3/2015 | Belson et al. |
| 2016/0015389 A1 | 1/2016 | Belson |
| 2017/0135692 A1 | 5/2017 | Belson et al. |

FOREIGN PATENT DOCUMENTS

| | | |
|---|---|---|
| WO | WO-9852473 A1 | 11/1998 |
| WO | WO-2007098212 A2 | 8/2007 |
| WO | WO-2007098212 A3 | 7/2008 |
| WO | WO-2009021161 A1 | 2/2009 |
| WO | WO-2010107698 A2 | 9/2010 |
| WO | WO-2011057299 A2 | 5/2011 |
| WO | WO-2011067770 A1 | 6/2011 |
| WO | WO-2011057299 A3 | 7/2011 |
| WO | WO-2011112721 A1 | 9/2011 |
| WO | WO-2011163666 A1 | 12/2011 |
| WO | WO-2013173366 A1 | 11/2013 |
| WO | WO-2016019349 A1 | 2/2016 |

OTHER PUBLICATIONS

Co-pending U.S. Appl. No. 15/009,642, filed Jan. 28, 2016.
"Office action dated Feb. 8, 2016 for U.S. Appl. No. 14/541,495."
Co-pending U.S. Appl. No. 14/732,719, filed Jun. 6, 2015.
Co-pending U.S. Appl. No. 14/801,853, filed Jul. 17, 2015.
European search report and opinion dated Jun. 14, 2013 for EP Application No. 10753932.2.
International search reoprt and written opinion dated Oct. 24, 2011 for PCT Application No. US2011/042036. Ci.
International search report and written opinion dated Aug. 19, 2013 for PCT Application No. US2013/040990.
International search report and written opinion dated Oct. 13, 2010 for PCT/US2010/027321.
Notice of allowance dated Mar. 10, 2015 for U.S. Appl. No. 13/224,666.
Notice of allowance dated Apr. 27, 2015 for U.S. Appl. No. 13/224,666.
Office action dated Jan. 2, 2014 for U.S. Appl. No. 13/273,000.
Office action dated Apr. 21, 2015 for U.S. Appl. No. 13/169,454.
Office action dated Apr. 30, 2015 for U.S. Appl. No. 14/541,495.
Office action dated Jun. 25, 2014 for U.S. Appl. No. 13/169,454.
Office action dated Jul. 16, 2014 for U.S. Appl. No. 13/273,000.
Office action dated Oct. 2, 2014 for U.S. Appl. No. 13/224,666.
Office action dated Dec. 30, 2013 for U.S. Appl. No. 13/169,454.
U.S. Appl. No. 14/541495, filed Nov. 14, 2014.
Notice of allowance dated Nov. 25, 2015 for U.S. Appl. No. 13/169,454.
Extended European Search Report and Search Opinion dated Jul. 6, 2017 for European Patent Application No. EP11799052.3.
"EP15827084.3 Extended Search Report dated Jan. 31, 2018".

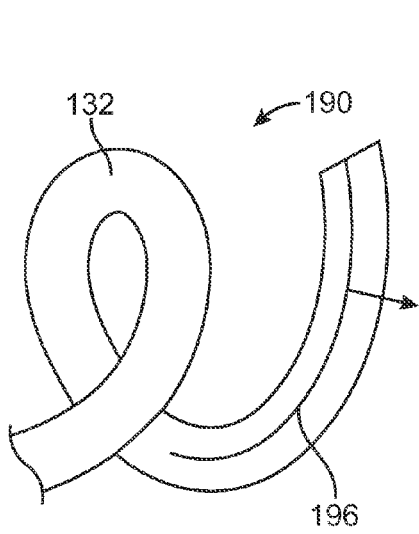
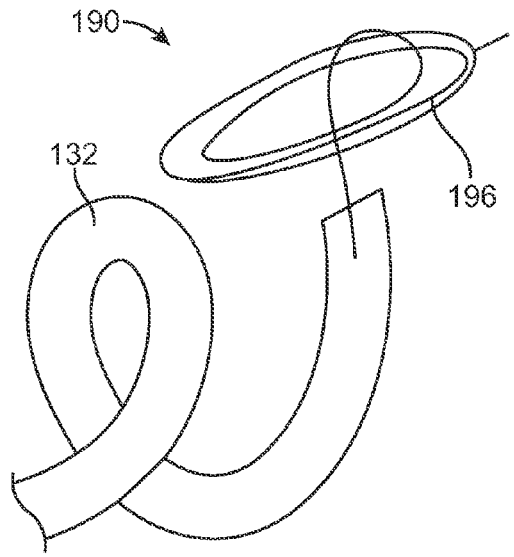
FIG. 31
FIG. 32
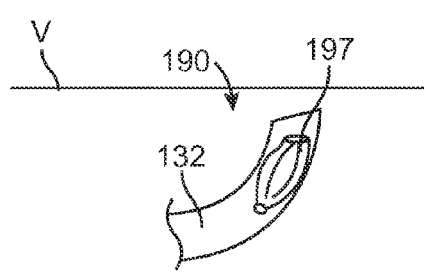
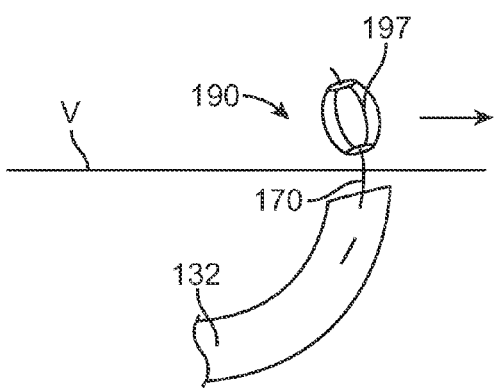
FIG. 33
FIG. 34
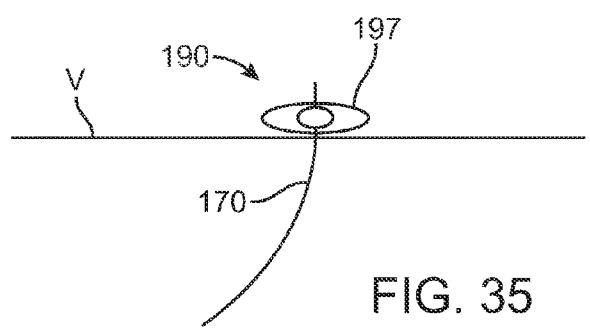
FIG. 35

VESSEL ACCESS AND CLOSURE DEVICE

CROSS-REFERENCES TO RELATED APPLICATIONS

This application is a divisional of U.S. patent application Ser. No. 13/224,666, now U.S. Pat. No. 9,078,633), filed Sep. 2, 2011, which is a continuation of International Patent Application No. PCT/US2010/027321, filed Mar. 15, 2010, which claims priority from U.S. Provisional application No. 61/210,018; filed on Mar. 14, 2009, the full disclosures of which are incorporated herein by reference in their entirety.

BACKGROUND OF THE INVENTION

Field of the Invention

The present invention relates to devices and methods for gaining percutaneous access to the lumen of a blood vessel and for subsequently closing the access site into the blood vessel. The invention is particularly advantageous for facilitating percutaneous vessel access and closure for large diameter interventional devices.

Minimally-invasive, catheter-based interventions have in many ways revolutionized the treatment of vascular disease. In many interventional procedures, an interventional device is introduced to the body through the patient's femoral artery or vein (percutaneous approach). The average diameter of the femoral artery in an adult patient is approximately 12 mm outside diameter and about 10 mm inside diameter. Each year, new interventional procedures become available for treating new indications. Some of these new interventional procedures require larger, more complex catheters. The larger the catheter or interventional device that is used, the more challenging it is to effectively close the opening in the blood vessel at the end of the procedure in order to avoid bleeding, hematomas and other complications. Vascular closure devices are available to facilitate vessel closure after procedures using smaller interventional devices, sizes 6-12 French (2-4 mm diameter). Above 12 French, it becomes particularly challenging to close the opening into the blood vessel. To date, no one has introduced a vascular closure device that is suitable for providing percutaneous access and for subsequently closing the access site into the blood vessel for interventional procedures using catheters in the range of 12-24 French (4-8 mm diameter). For this reason, many interventional procedures using larger catheters rely on a vessel cutdown to access the vein or artery. Using a surgical cutdown to access the blood vessel undermines the minimally-invasive aspect of the interventional procedure.

Therefore, what is much needed and has heretofore been unavailable are devices and methods for facilitating percutaneous access to the lumen of a blood vessel and for subsequently closing the access site into the blood vessel that are suitable for use with large diameter interventional devices.

BRIEF SUMMARY OF THE INVENTION

To satisfy this unmet clinical need, the present invention provides a vessel access and closure device that places a running suture in the wall of a blood vessel and creates an access site through the wall of the blood vessel in the area bounded by the running suture. Optionally, an introducer sheath may be placed through the access site into the vessel lumen. One or more interventional devices may be inserted directly through the access site or through the introducer sheath for performing an interventional procedure within the patient's vascular system. Once the interventional procedure has been completed, the interventional devices and the introducer sheath are withdrawn and the running suture is tightened to close the access site into the vessel. A suture lock or a knot may be used to lock the running suture.

The vessel access and closure device utilizes a rotating helical suture needle that carries a suture along a helical path through the wall of the blood vessel. When the direction of rotation reverses, a suture anchor attached to a distal end of the suture is released, anchoring the suture to the vessel wall. A loose helical coil of suture is left behind as the helical suture needle withdraws. The vessel access and closure device is withdrawn and replaced with a vessel dilator and an introducer sheath that opens up a larger access opening into the blood vessel and creates a pathway for introduction of interventional device into the blood vessel. Alternatively, the vessel dilator and introducer sheath may be integrated with the vessel access and closure device.

The vessel access and closure device described herein could also be used to close other tubular organs (intestine, esophagus, airways, etc.) and also non tubular organs (abdominal fascia, etc.).

BRIEF DESCRIPTION OF THE DRAWINGS

FIGS. 31 and 32 show a distal portion of a tubular helical suture needle with a suture anchor made of a superelastic or shape memory NiTi alloy wire.

FIGS. 33, 34 and 35 show a distal portion of a tubular helical suture needle with a suture anchor configured as an expandable cage.

DETAILED DESCRIPTION OF THE INVENTION

Figure 1:
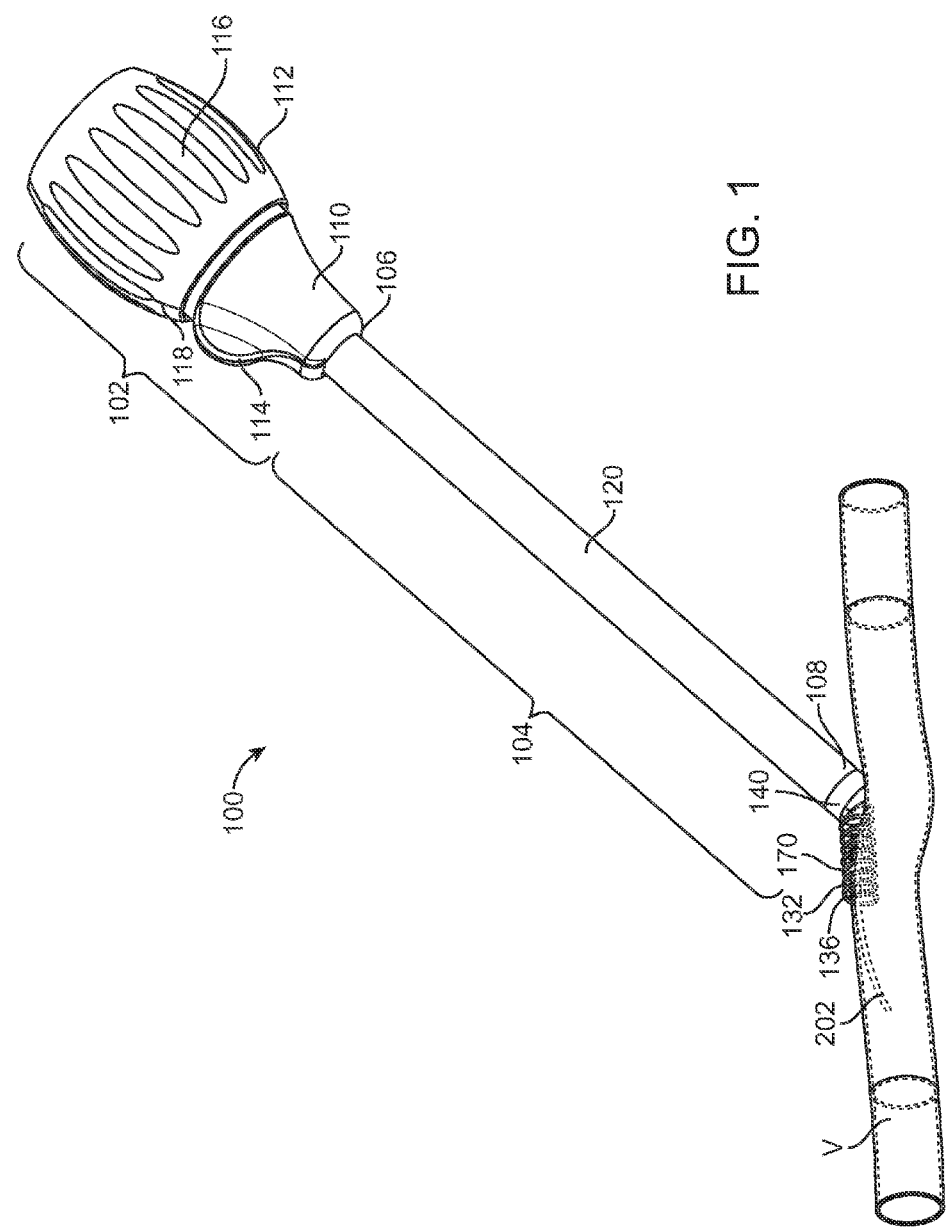
FIG. 1 is a perspective view of a vessel access and closure device according to the present invention shown in a partially deployed position.
Figure 2:
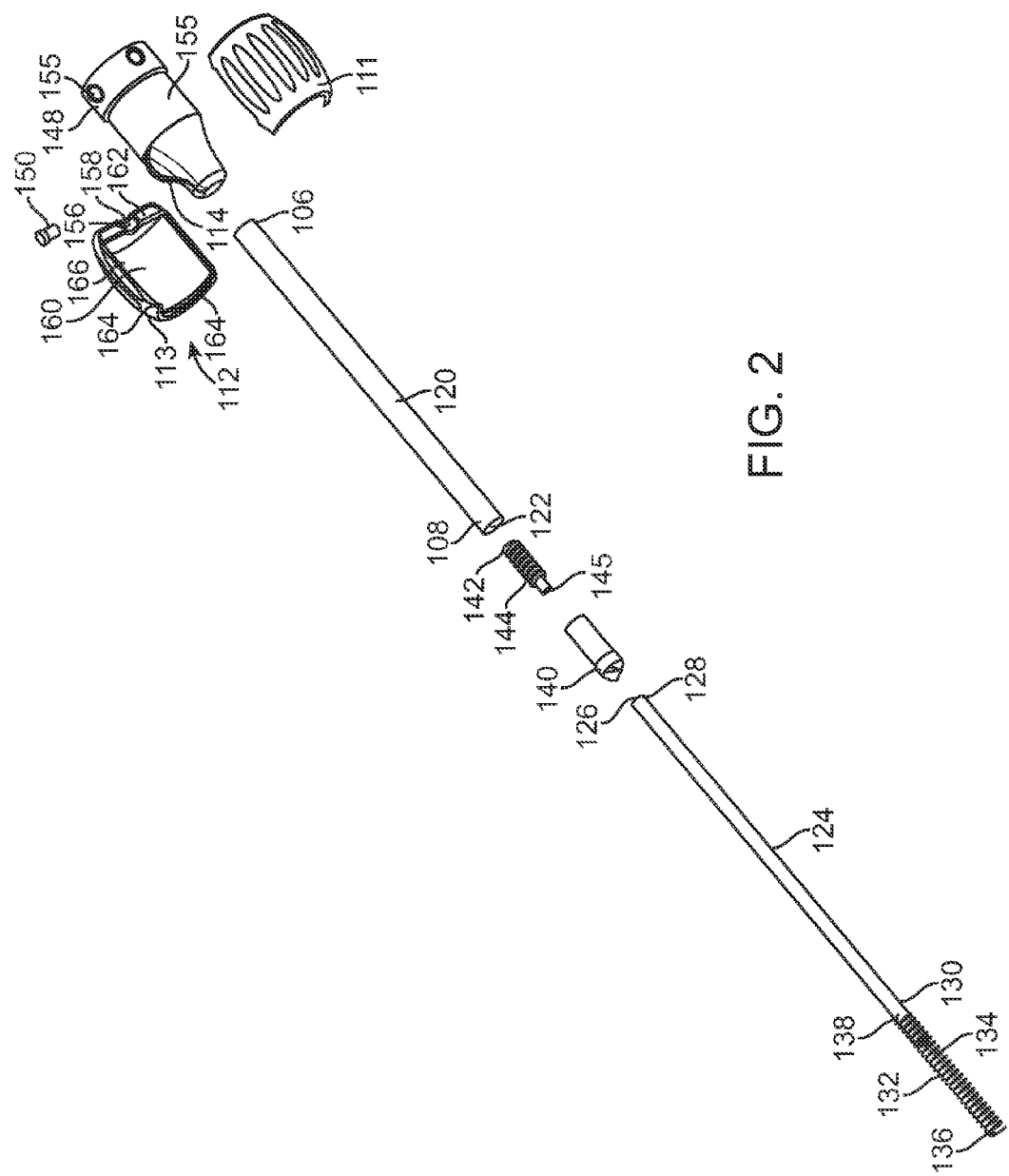
FIG. 2 is an exploded view of the vessel access and closure device of FIG. 1.
Figure 3:
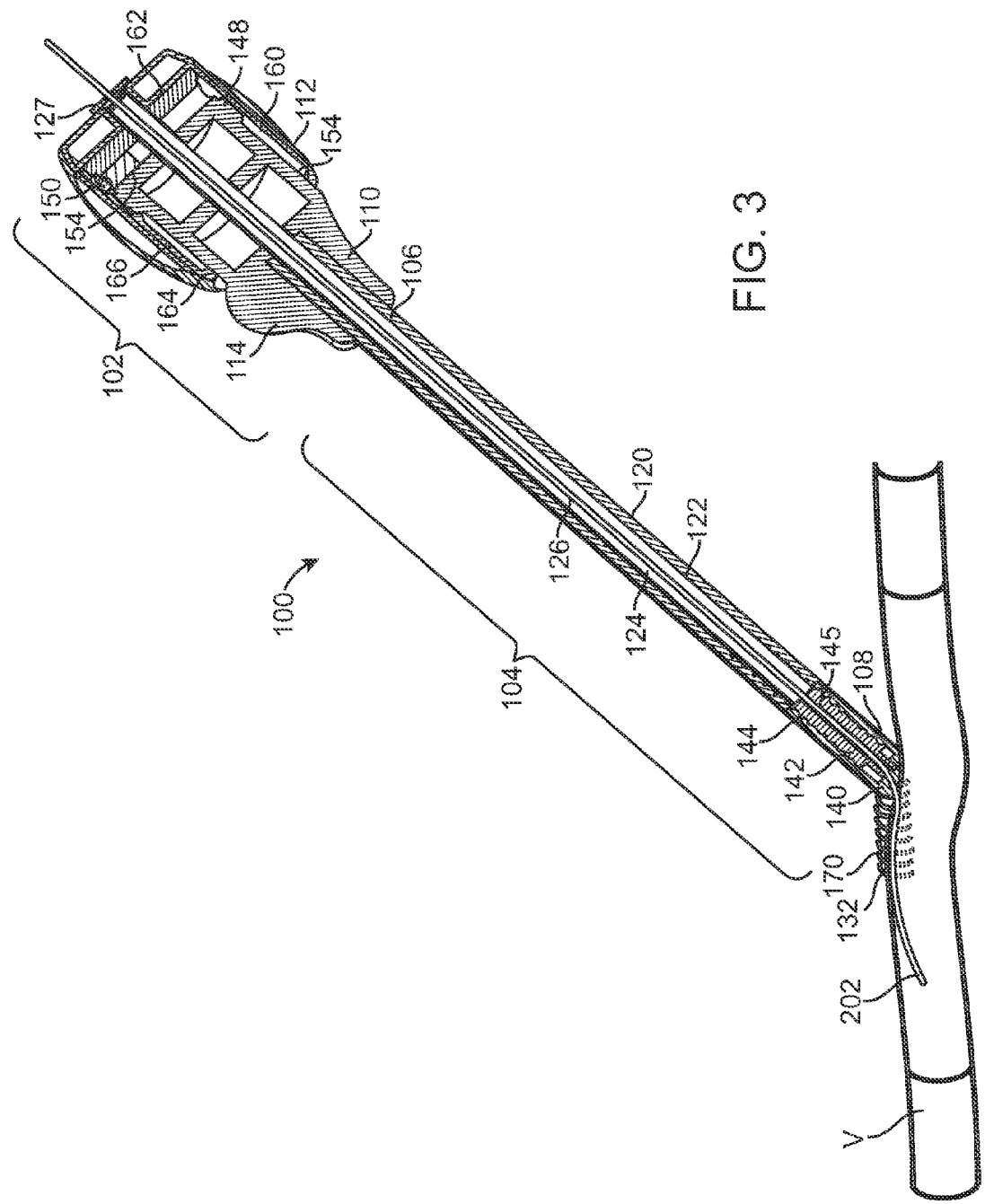
FIG. 3 is cutaway view showing the internal structure of the vessel access and closure device of FIG. 1.

FIG. 1 is a perspective view of a vessel access and closure device 100 according to the present invention shown in a partially deployed position for placing a running suture in the wall of a blood vessel V. FIG. 2 is an exploded view of the vessel access and closure device 100 of FIG. 1. FIG. 3 is cutaway view showing the internal structure of the vessel access and closure device 100 of FIG. 1.

The vessel access and closure device 100 has an elongated shaft portion 104 with a proximal end 106 and a distal end 108. A proximal handle 102 is connected to the elongated shaft portion 104 at the proximal end 106. The proximal handle 102 has a stationary portion 110 and a rotating portion 112 located proximal to the stationary portion 110. Preferably, the rotating portion 112 of the proximal handle 102 will have a contour 116 and/or texture configured for easy gripping by the operator for applying torque to rotate the rotating portion 112. Additionally, the rotating portion 112 may have a line 118 or other marking to indicate the rotational position of the rotating portion 112. Preferably, the stationary portion 110 of the proximal handle 102 is configured with a wing-shaped raised portion 114, preferably located at a 12 o'clock position on the closure device 100, that serves as a handle to apply torque to resist rotation of the device 100 when the rotating portion 112 is rotated and as a visual and tactile indicator to the operator of the device orientation.

As shown in FIG. 2, the elongated shaft portion 104 has a hollow, tubular outer shaft 120 with an inner lumen 122 that, when assembled as in FIG. 3, is fixed at its proximal end 106 to the stationary portion 110 of the proximal handle 102. Positioned within the inner lumen 122 of the outer shaft 120 is a hollow, tubular inner shaft or torque tube 124 with a central lumen 126 that, when assembled, is fixed at its proximal end 128 to the rotating portion 112 of the proximal handle 102. Preferably, the outer shaft 120 and the torque tube 124 are each constructed of stainless steel tubing or, alternatively, another metal, such as a titanium or cobalt-chromium alloy, a rigid polymer or a reinforced polymer composite. A helical suture needle 132 having a multiplicity of helical turns or coils is connected at its proximal end 138 to the distal end 130 of the torque tube 124. The helical suture needle 132 has a central passage 134 that is axially aligned with the central lumen 126 of the torque tube 124. For ease of manufacture and assembly, the helical suture needle 132 will preferably have an outer diameter that is approximately the same as the outer diameter of the torque tube 124. The helical suture needle 132 is configured to carry a suture thread along the helical coil. For this purpose, the helical suture needle 132 may be hollow or it may be solid, but with a groove or channel to carry the suture, as will be discussed in greater detail below. Preferably, the helical suture needle 132 is constructed of a metal, such as stainless steel or a titanium, nickel-titanium or cobalt-chromium alloy. The distal end 136 of the helical suture needle 132 will typically be sharpened into a tissue-penetrating point, however other possible configurations are described below.

A specially contoured suturing tip 140 is attached at the distal end 108 of the outer shaft 120 and proximal to it, inside the inner lumen 122 of the outer shaft 120, is attached a needle guide 142 with a helical groove 144 on its exterior having approximately the same diameter and pitch as the helical suture needle 132. A guidewire lumen 145 extends through the center of the needle guide 142 and aligns with the central lumen 126 of the torque tube 124. Preferably, a hemostasis valve 127, such as an elastic membrane with a hole or slit through it, is provided at the proximal end of the handle 102 to prevent excessive bleeding through the central lumen 126. The hemostasis valve 127 provides a sliding seal for insertion of the guidewire 202 and, optionally, for the positioning member 242, dilator 210 and/or introducer sheath 222 described below. The needle guide 142 and the suturing tip 140 do not rotate with respect to the outer shaft 120. The needle guide 142 may be attached to or integral with the suturing tip 140 or it may be attached directly to the outer shaft 120. When assembled, the helical suture needle 132 rides in the helical groove 144 of the needle guide 142. Alternatively, the needle guide 142 may be made without the helical groove 144.

The stationary portion 110 of the proximal handle 102 is preferably made of a rigid polymer material, such as polycarbonate, nylon, ABS, polyurethane, etc., and may be molded as one piece or two and assembled onto the proximal end 106 of the outer shaft 120 by insert molding, compression, adhesives, pins, set screws, keys, splines or any other secure method. In the example shown, the proximal end 106 of the outer shaft 120 is inserted into a cylindrical pocket 146 in distal end of the stationary portion 110 of the proximal handle 102 and secured with adhesive. The stationary portion 110 of the proximal handle 102 has a cylindrical portion 154 and an annular boss 148 that is just slightly larger in diameter than the cylindrical portion 154. A ball detent 150 or the like is inserted into a transverse hole 155 in the annular boss 148, preferably located at a 12 o'clock position.

For ease of manufacture and assembly, the rotating portion 112 of the proximal handle 102 is preferably molded as two pieces 111, 113 and assembled onto the proximal end 128 of the torque tube 124 and the stationary portion 110 of the proximal handle 102 at the same time. The two pieces 111, 113 of the rotating portion 112 may be joined together by adhesives, screws, etc. The proximal end 128 of the torque tube 124 fits into a central bore 156 at the proximal end of the rotating portion 112 of the proximal handle 102 and is secured by an adhesive. Optionally, an annular ridge 158 may be molded at the proximal end of the central bore 156 to assure proper axial positioning of the torque tube 124 during assembly. During assembly, the line 118 on the rotating portion 112 is axially aligned with the distal end 136 of the helical suture needle 132.

The rotating portion 112 of the proximal handle 102 has an internal cylindrical portion 160 that is delineated on the proximal end by the proximal wall 162 of the rotating portion 112 of the proximal handle 102 and on the distal end by an inwardly projecting annular flange 164. The internal cylindrical portion 160 has an inner diameter that is just slightly larger than the outer diameter of the annular boss 148 on the stationary portion 110 of the proximal handle 102. The inwardly projecting annular flange 164 has an inner diameter that is just slightly larger than the outer diameter of the cylindrical portion 154 of the stationary portion 110 of the proximal handle 102, but slightly smaller than the annular boss 148. Thus, the rotating portion 112 of the proximal handle 102 is able to rotate and move axially on the stationary portion 110, but the axial movement in the proximal direction is limited by the inwardly projecting annular flange 164 and in the distal direction by the proximal wall 162 of the rotating portion 112.

A longitudinal groove 166 is molded into the internal cylindrical portion 160 of the rotating portion 112 of the proximal handle 102, preferably located at a 12 o'clock position where the two pieces 111, 113 of the rotating portion 112 join. The longitudinal groove 166 interacts with the ball detent 150 each time it rotates past the 12 o'clock position to give an audible and/or tactile indication to the operator that the rotating portion 112, and hence the distal end 136 of the helical suture needle 132 also, is rotating past the 12 o'clock position.

As the rotating portion 112 of the proximal handle 102 rotates in the direction of the helix of the helical suture needle 132 (clockwise in the example shown), the helical suture needle 132 engages the helical groove 144 on the needle guide 142, moving the helical suture needle 132, the torque tube 124 and the rotating portion 112 distally with respect to the outer shaft 120 and the stationary portion 110 of the proximal handle 102.

In an alternative configuration, the rotating portion 112 of the proximal handle 102 may be molded as a single piece that is threaded onto the stationary portion 110 of the proximal handle 102. The screw threads between the rotating portion 112 and the stationary portion 110 will preferably have a pitch that is equal to the pitch or coil-to-coil distance of the helical suture needle 132 so that the rotating portion 112 will advance and retract synchronously with the helical suture needle 132. This configuration controls the axial movement of the rotating portion 112 with respect to the stationary portion 110 and obviates the need for the annular boss 148 and the inwardly projecting annular flange 164 described above.

Figure 4:
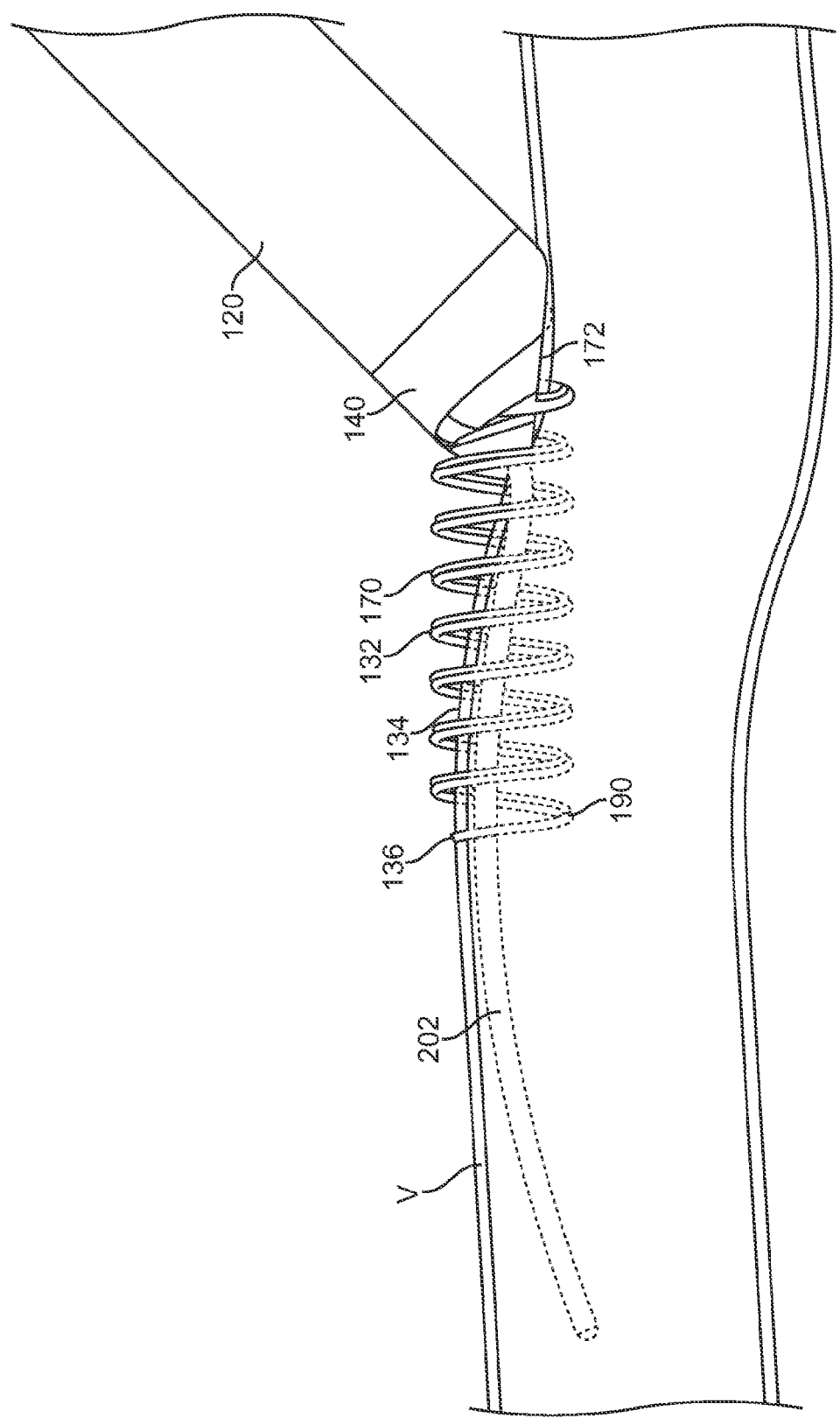
FIGS. 4, 5 and 6 show close up views of the distal end of the vessel access and closure device, showing how the helical suture needle with the suture on it emerges from the suturing tip and passes through the wall of the blood vessel.
Figure 5:
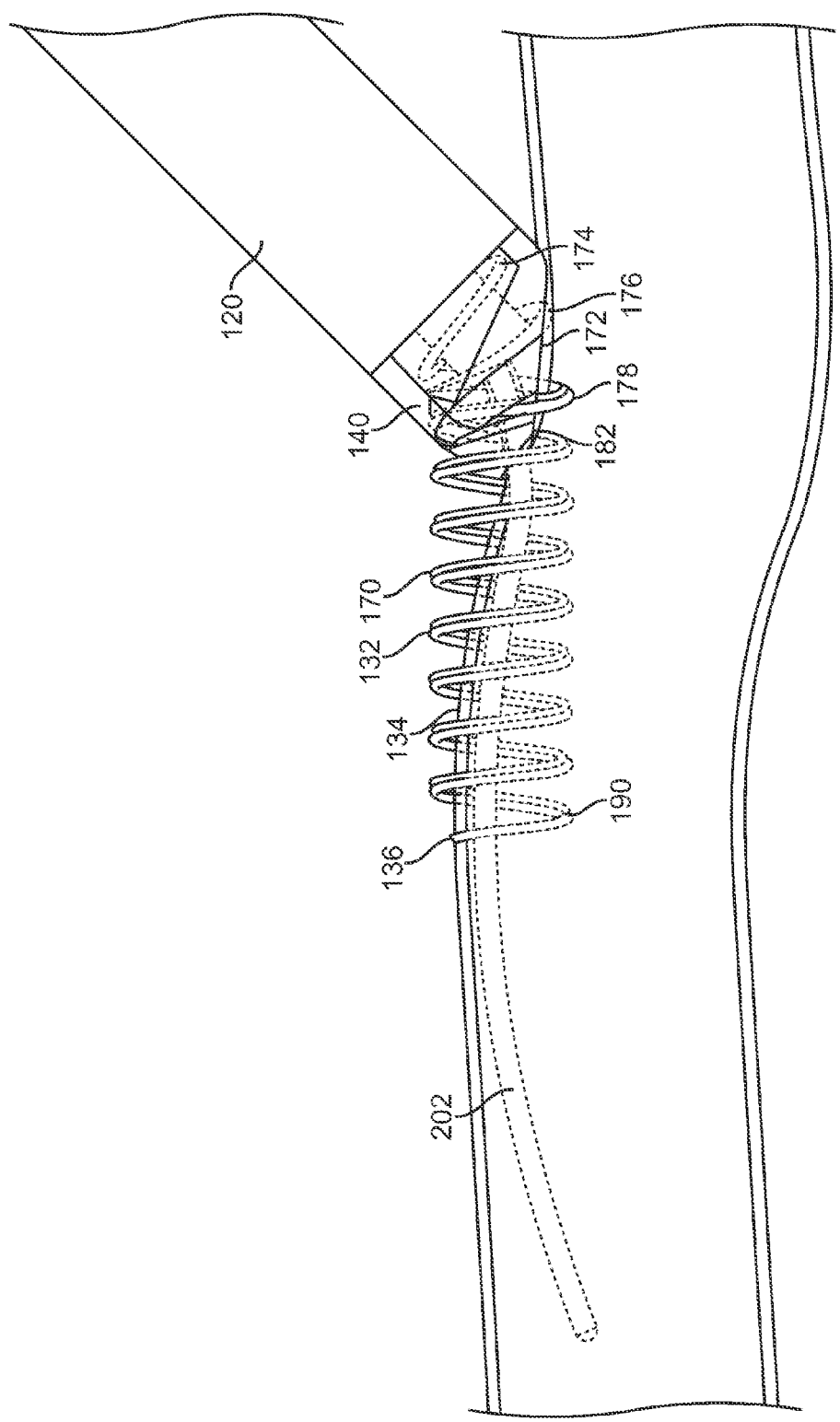
Figure 6:
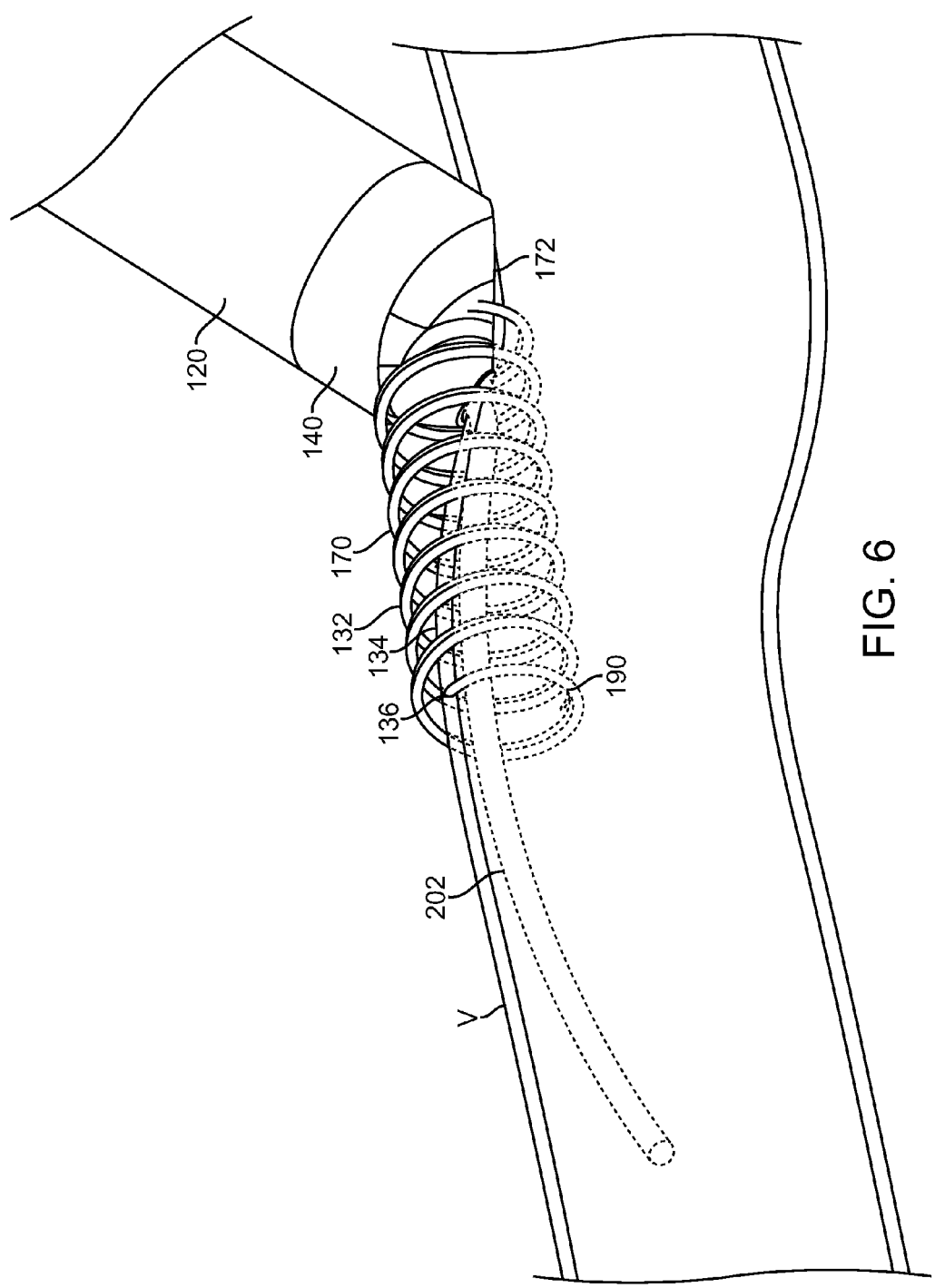

FIGS. 4, 5 and 6 show close up views of the distal end of the vessel access and closure device 100, showing how the helical suture needle 132, with the suture 170 on it, emerges from the suturing tip 140 and passes through the wall of the blood vessel V. The suturing tip 140 has a distal face 172 that is at an angle of approximately 45 degrees from the longitudinal axis of the elongated shaft portion 104. In other embodiments, this angle can be from 15 to 135 degrees. The distal face 172 of the suturing tip 140 may be flat or it may have a curvature that is a section of a cylinder with a radius of curvature approximately equal to the radius of the blood vessel V that it is intended to be used with. The suturing tip 140 is configured so that it gradually redirects the helical suture needle 132 from its orientation inside of the closure device 100 where the helical suture needle 132 is concentric with the longitudinal axis of the elongated shaft portion 104 to an orientation where the helical suture needle 132 is concentric with an axis that is at an angle of approximately 45 degrees from the longitudinal axis of the elongated shaft portion 104. FIG. 5, which shows a phantom view of the suturing tip 140, illustrates how this is accomplished. The interior of the suturing tip 140 defines a curving helical path that gradually redirects the helical suture needle 132 over a course of 2-3 turns of the helical coil. In FIG. 5, coil 174 is concentric with the longitudinal axis of the elongated shaft portion 104. Coil 176 has been skewed approximately 15-30 degrees from coil 174 and coil 178 has been skewed another approximately 15-30 degrees from coil 176. Coil 180 and the remainder of the coils distal to it are approximately concentric with an axis that is at an angle of approximately 45 degrees from the longitudinal axis of the elongated shaft portion 104. Another way to envision this geometry is that the transitional coils 174, 176, 178 are bunched up together on the inside of the curve, which causes the helical suture needle 132 to change direction by approximately 45 degrees. Another feature of the suturing tip 140 is that coils 174 and 176 are entirely inside of the suturing tip 140, whereas coil 178 is exposed along approximately one half or a turn so that the distal end 136 of the helical suture needle 132 can take a first bite of the vessel wall V for placing the suture 170 as it rotates past this position. Coil 180 and the remainder of the coils distal to it are entirely exposed for additional bites of the vessel wall V.

A guidewire lumen 182 passes through the suturing tip 140 making a gradual bend of approximately 135 degrees to emerge approximately parallel to the distal face 172 of the suturing tip 140. When the device 100 is assembled, the proximal end of the guidewire lumen 182 of the suturing tip 140 aligns with the guidewire lumen 145 of the needle guide 142 and the central lumen 126 of the torque tube 124.

Another important feature of the vessel access and closure device 100 is a suture anchor 190 that is connected to the distal end of the suture 170. Various forms of the suture anchor 190 are shown in FIGS. 25-35. Initially, the suture anchor 190 is located at or near the distal end 136 of the helical suture needle 132. The suture anchor 190 is configured so that, as the helical suture needle 132 moves through the vessel wall in the distal direction, the suture anchor 190 moves smoothly forward without catching on the tissue, however, when the direction of the helical suture needle 132 is reversed, the suture anchor 190 opens or spreads and anchors the distal end of the suture 170 to the vessel wall. The helical suture needle 132 leaves a loose helical coil of suture 170 in the vessel wall as it is withdrawn. Release of the suture 170 from the helical suture needle 132 may be passive or active.

Figure 7:
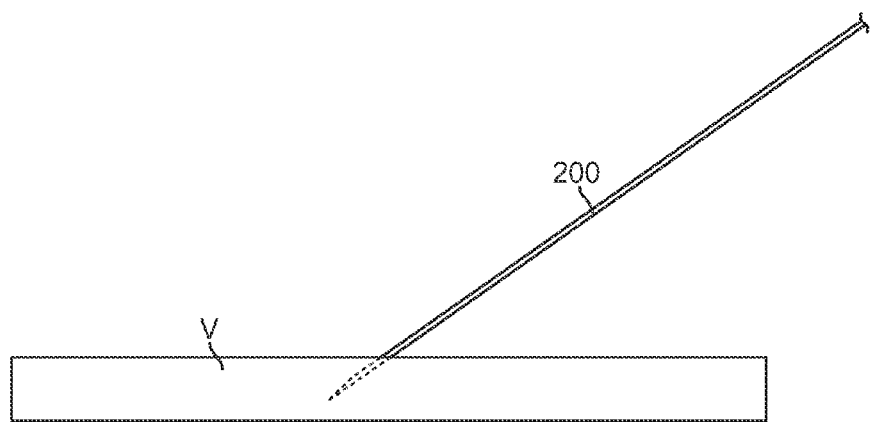
FIGS. 7-22 illustrate a method of using the vessel access and closure device to open a pathway into the lumen of a blood vessel and subsequently to close the point of entry into the blood vessel.

FIGS. 7-22 illustrate a method of using the vessel access and closure device 100 to open a pathway into the lumen of a blood vessel V and subsequently to close the point of entry into the blood vessel V. This method, and variations of it, may be performed with any of the embodiments of the vessel access and closure device 100 described herein. The method is initiated using the Seldinger technique to access the lumen of the blood vessel V, which may be an artery or a vein. As shown in FIG. 7, an access needle 200 is used to puncture the patient's skin and create a tract through the tissue and into the lumen of the blood vessel V. Optionally, a skin nick may be made with a scalpel before or after inserting the access needle 200 to prevent tearing of the patient's skin later in the procedure. Preferably, the needle puncture is made at an angle of approximately 30 to 45 degrees from the central axis of the blood vessel V. Blood flashback through the access needle 200 may be used to verify that the distal tip of the access needle 200 is in the lumen of the blood vessel V and whether an artery or vein has been correctly accessed. (For clarity, the patient's skin and the tissue surrounding the blood vessel V have been left out of these illustrations.)

Figure 8:
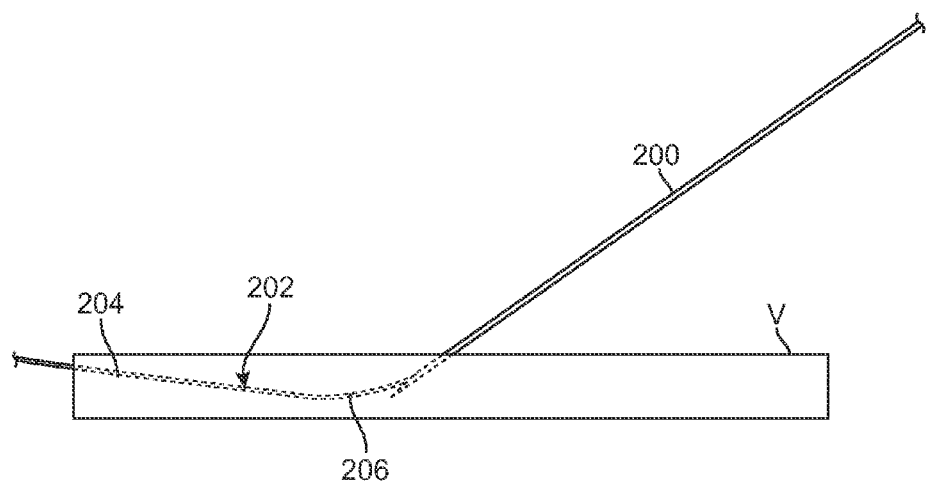
Figure 9:
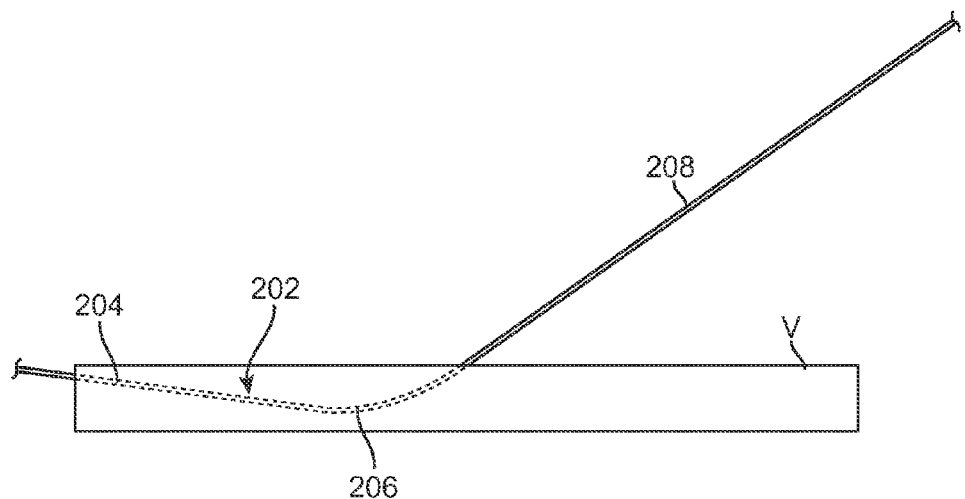

Next, a special guidewire 202 is inserted through the access needle 200 into the lumen of the blood vessel V, as shown in FIG. 8. The guidewire 202 has a bend 206 of approximately 135 degrees between a distal portion 204 and a proximal portion 208 that is used to locate the wall of the blood vessel V during subsequent steps of the method. Optionally, the guidewire 202 may have a J-shaped tip to avoid potential injury to the interior of the blood vessel, as is known in the art. The operator can feel when the bend 206 in the guidewire 202 has exited the distal tip of the access needle 200 and entered the lumen of the blood vessel V, as shown in FIG. 8. At this point the access needle 200 is withdrawn, leaving the guidewire 202 to maintain a pathway through the tissue tract created by the access needle 200 and into the lumen of the blood vessel V, as shown in FIG. 9.

Optionally, the tissue tract can be dilated using a series of tapered dilators or using an expandable dilator, such as an inflatable balloon, as is know in the art. Whether this step is necessary, depends in part on how large the tissue tract needs to be and how resistant the tissue is to passage of the shaft portion 104 of the vessel access and closure device 100. In an alternative method, a tissue cutdown can be used to access the exterior of the blood vessel V before inserting the access needle 200.

Figure 10:
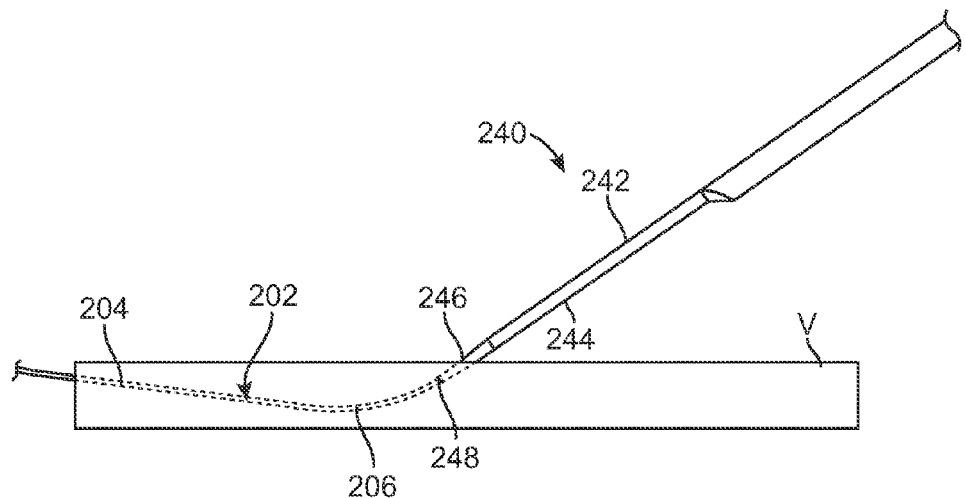
Figure 11:
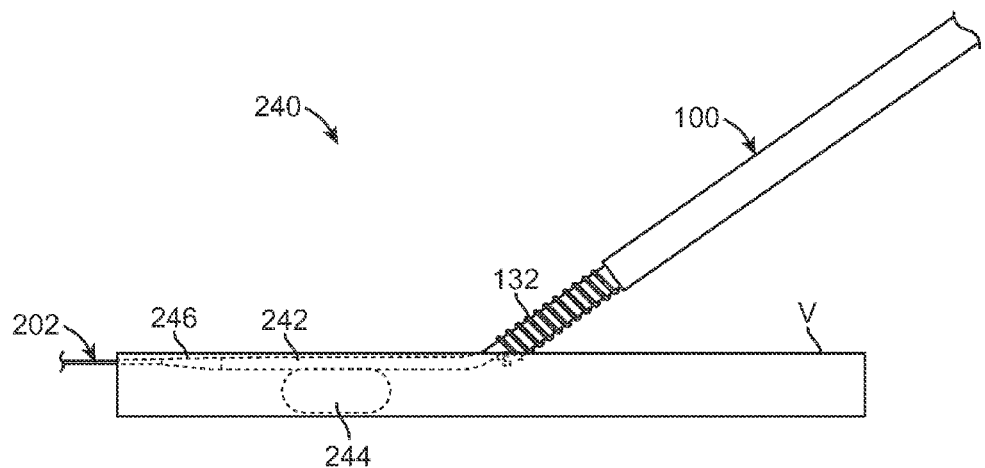

Next, the proximal portion 208 of the guidewire 202 is inserted into the guidewire lumen 182 in the suturing tip 140 and through the guidewire lumen 145 of the needle guide 142 and the central lumen 126 of the torque tube 124 to emerge from the proximal handle 102. The shaft portion 104 of the vessel access and closure device 100 is advanced through the tissue tract while pulling upward gently on the guidewire 202 to position the bend 206 of the guidewire 202 at the wall of the blood vessel V, as shown in FIG. 10. The operator will be able to feel when the shaft portion 104 of the device 100 has reached the blood vessel V and the distal face 172 of the suturing tip 140 is against the exterior of the vessel wall, as shown in FIG. 11. Proper positioning of the suturing tip 140 can be verified fluoroscopically or with ultrasound imaging.

Figure 12:
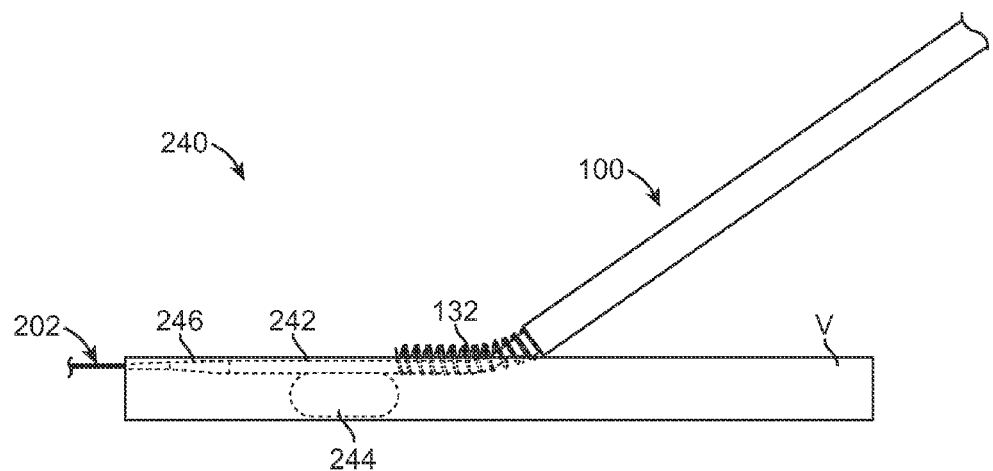

As shown in FIGS. 10, 11 and 12, the apparatus may optionally include an additional positioning device 240 that helps to assure that the suture is placed in the near wall of the blood vessel V as intended. The positioning device 240 may be a separate device insertable through the vessel access and closure device 100 or it may be integrated into vessel access and closure device 100. The positioning device 240 has an elongated tubular guiding element 242 with a guidewire lumen 248 that is sized to fit over the guidewire 202. The guiding element 242 has a tapered dilating tip 246 at its distal end and a biasing element in the form of an inflatable balloon 244 mounted on one side of the guiding element 242. An inflation lumen connected to the balloon 244 extends through the guiding element 242 to a proximal hub (not shown) on the proximal end of the guiding element 242. Preferably, the balloon 244 has a very low deflated profile, as shown in FIG. 10, so that it can fit through the lumens 182, 145, 126 in the elongated shaft portion 104 of the vessel access and closure device 100. The balloon 244 is preferably located at a 6 o'clock position on the guiding element 242. A line or other mark (not shown) at a 12 o'clock position on the proximal end of the guiding element 242 allows the operator to properly orient the balloon 244 during insertion. The inflated profile may be cylindrical, as shown in FIG. 11, or it may be spheroidal or other shapes described herein. The balloon 244 may be made of compliant or noncompliant material. The diameter of the inflated balloon 244 is such that it biases the guiding element 242 toward the near wall of the blood vessel V, so that the helical suture needle 132 will be properly oriented with respect to the blood vessel wall when it is advanced, as shown in FIG. 12.

Optionally, the positioning device 240 may also include a needle guide 241 on the guiding element 242 proximal to the balloon 244. The needle guide 241 has a diameter that is larger than the diameter of the guiding element 242 and is eccentrically positioned on the guiding element 242, as best seen in FIG. 10. The needle guide 241 may be cylindrical or it may have an elliptical or D-shaped cross section. The needle guide 241 assures that the helical suture needle 132 will be properly aligned with the wall of the blood vessel V when it is advanced. The eccentric positioning of the needle guide 241 allows the helical suture needle 132 to take at least one, and more preferably two bites, of the blood vessel wall proximal to the puncture site, as shown in FIGS. 11 and 12.

The rotating portion 112 of the proximal handle 102 is rotated clockwise like a knob while holding the stationary portion 110 to prevent it from rotating. The torque tube 124 transfers the rotation to the helical suture needle 132 which engages the helical groove 144 on the needle guide 142 and advances distally, as shown in FIG. 12. The proximal handle 102 may include a visual indication of the position of the stationary portion 110 with respect to the rotating portion 112 and/or a counter for recording the number of turns as an indication of the position of the helical suture needle 132. As can be seen in FIG. 4, the first two stitches or bites of the vessel wall made by the helical suture needle 132 are proximal to the point where the guidewire 202 enters the vessel wall. Approximately 4 to 8 more stitches are made distal to the point where the guidewire 202 enters the vessel wall.

Figure 13:
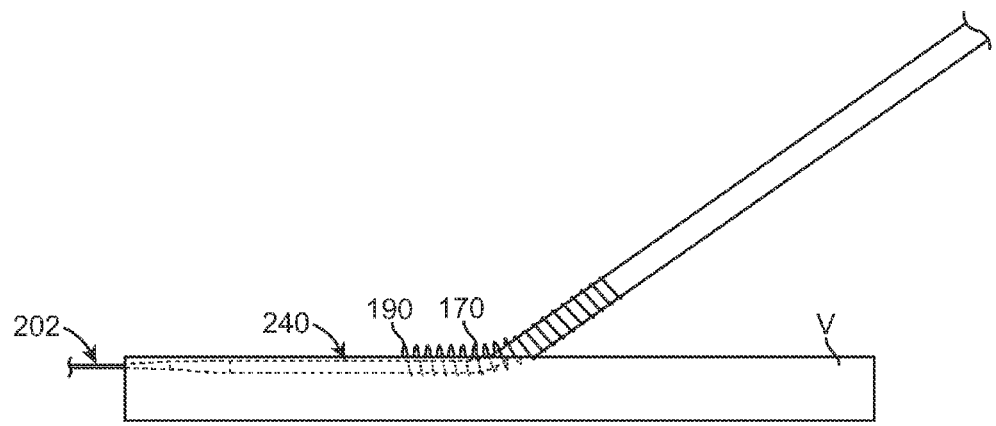

After a sufficient number of stitches have been placed, the clockwise rotation is stopped, preferably when the distal end 136 of the helical suture needle 132 and the suture anchor 190 are at approximately the 12 o'clock position outside of the blood vessel V. The rotating portion 112 of the proximal handle 102 is then rotated counterclockwise to withdraw the helical suture needle 132. The suture anchor 190 engages the vessel wall and prevents the suture 170 from backing out. A loose helical coil of suture 170 is left behind as the helical suture needle 132 withdraws, as shown in FIG. 13.

Figure 14:
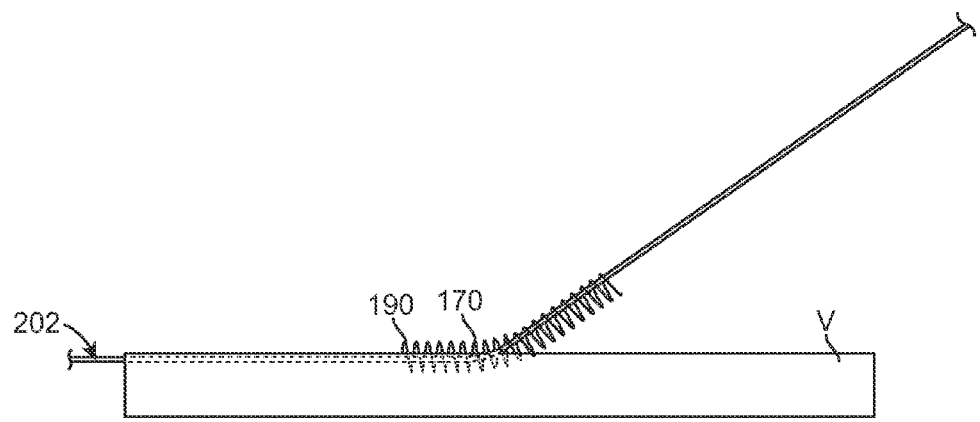

The vessel access and closure device 100 is withdrawn from the tissue tract leaving the helical coil of suture 170 in the vessel wall and the guidewire 202, which maintains a pathway through the tissue tract and through the center of the helical coil of suture 170, as shown in FIG. 14.

At this point, there are a number of options in the procedure. An interventional device may be introduced directly over the guidewire 202, through the tissue tract and into the lumen of the blood vessel V. This option is feasible when the interventional device has a smoothly tapered distal end that will pass through the vessel wall by gradually dilating the puncture site. The diameter of the interventional device would preferably be smaller than the diameter of the helical coil of suture 170 so that it could easily pass through the coil into the lumen of the blood vessel V. (Alternatively, a stretchable or extendable suture, as described herein below, would allow an interventional device that is actually larger in diameter than the helical coil of suture 170 to pass through.) An example of a device suitable for this variation of the method would be a large dilatation balloon, such as a valvuloplasty balloon. Another option is to insert an introducer sheath with a coaxial dilator over the guidewire 202, through the tissue tract and into the lumen of the blood vessel V. An introducer sheath allows interventional devices that might have a more a complex geometry with projections that might otherwise catch or snag on the suture 170 or the vessel wall to be easily passed through the puncture site into the lumen of the blood vessel V. An example of a device suitable for this variation of the method would be a stent graft for repair of abdominal aortic aneurysms. For interventional devices requiring a large diameter introducer sheath it may not be sufficient to simply dilate the puncture through the vessel wall because the vessel wall might tear rather than gradually dilate as intended. An example of a device that might require a large diameter introducer sheath might be a catheter for implanting a stented percutaneous aortic valve replacement. For this situation, the present invention includes, as an option, a cutting or scoring dilator 210 that is illustrated in FIGS. 15 and 16.

The cutting or scoring dilator 210 has a tapered dilating tip 212 on the distal end of a cylindrical body. A cutting or scoring element 214 located on one side of the tapered portion 212. The cutting or scoring element 214 is oriented longitudinally on the dilator 210 and is preferably located at a 12 o'clock position. A line or other mark on the proximal end of the dilator 210 indicates the orientation of the cutting or scoring element 214 to the operator. The cutting or scoring element 214 may be configured as a sharp cutting blade that actually cuts the vessel wall along a longitudinal line or it may be a wire, a wedge or a raised ridge that causes a stress riser in the vessel wall so that it preferentially splits or tears along a longitudinal line as the puncture site is dilated. Preferably, the cutting or scoring element 214 does not extend to the full outer diameter of the dilator 210, so that last bit of the insertion site through the vessel wall is dilated rather than cut or split. This provides better hemostasis at the insertion site and, in the case of a cutting or scoring element 214 configured as a sharp cutting blade, prevents the blade from cutting the helical coil of suture 170 that is in place. Alternatively or in addition, the cutting or scoring element 214 may have an electrocautery or electrocoagulation capability. Optionally, the cutting or scoring dilator 210 may also have a flexible lead section 216 that is smaller in diameter extending distally from the tapered dilating tip 212. The flexible lead section 216 improves the ability of the cutting or scoring dilator 210 to follow the guidewire 202 around the bend 206 into the lumen of the blood vessel V. A guidewire lumen 220 extends through the flexible lead section 216 and the body 218 of the cutting or scoring dilator 210. Alternatively, the cutting or scoring element 214 may be located on this flexible lead section 216. Preferably, a thin-walled introducer sheath 222 is positioned coaxially around the body 218 of the cutting or scoring dilator 210. Alternatively, a thin-walled introducer sheath 222 can be collapsed flat and introduced beside the body 218 of the cutting or scoring dilator 210. The introducer sheath 222 would be opened up to its full diameter after the dilator 210 has been withdrawn.

Figure 15:
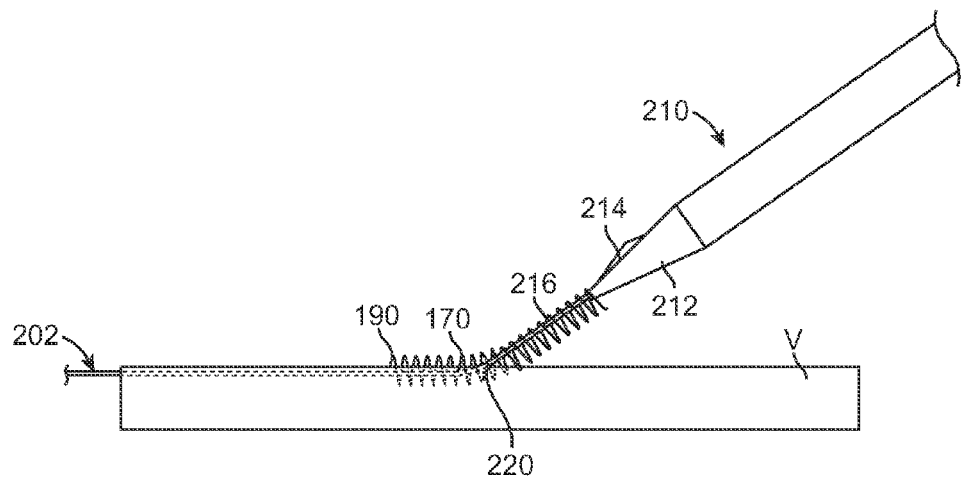
Figure 16:
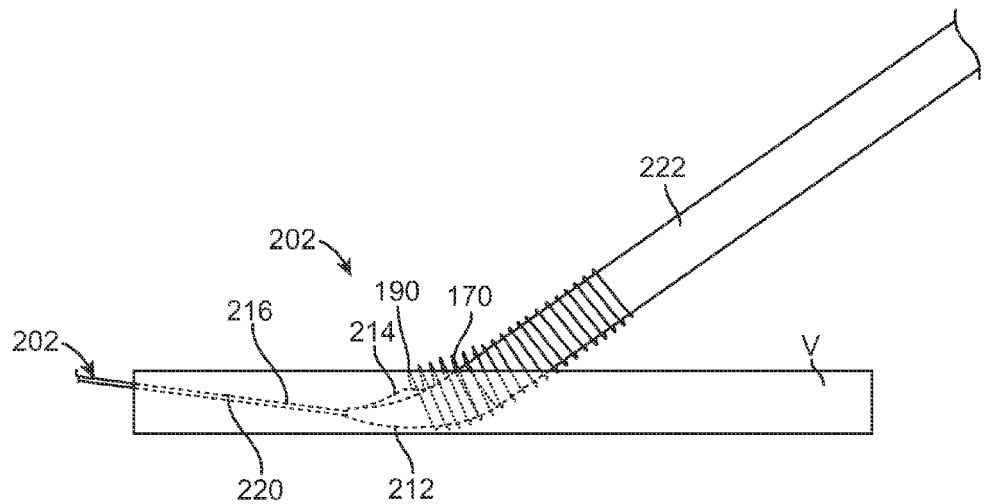

FIG. 15 shows the cutting or scoring dilator 210 following the guidewire 202 through the tissue tract. The distal tip of the flexible lead section 216 is positioned to enter the puncture site through the vessel wall. FIG. 16 shows the cutting or scoring dilator 210 with the tapered portion 212 inside the lumen of the blood vessel V. By a combination of cutting, tearing or splitting and dilating, the cutting or scoring dilator 210 has enlarged the puncture site to an insertion site large enough for the introducer sheath 222. The cutting or scoring dilator 210 also passes through the helical coil of suture 170 and may optionally dilate it to a larger diameter.

Figure 17:
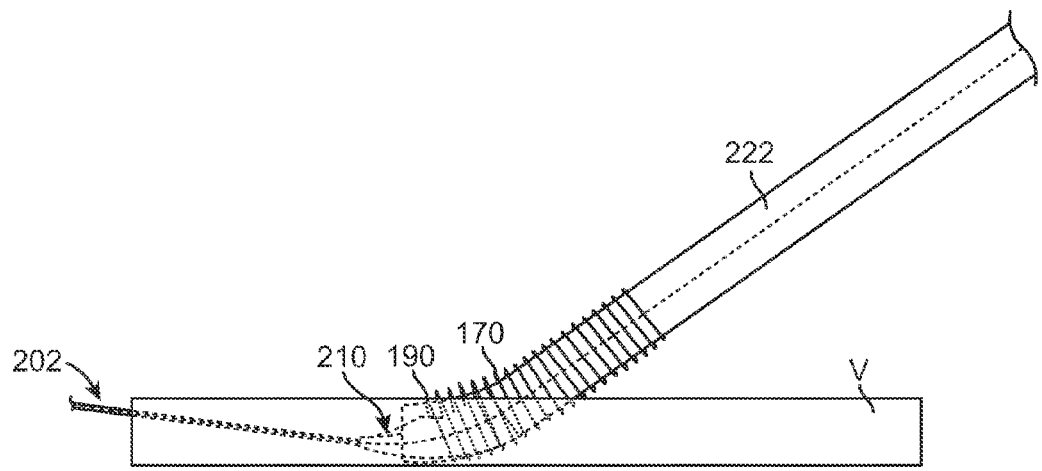
Figure 18:
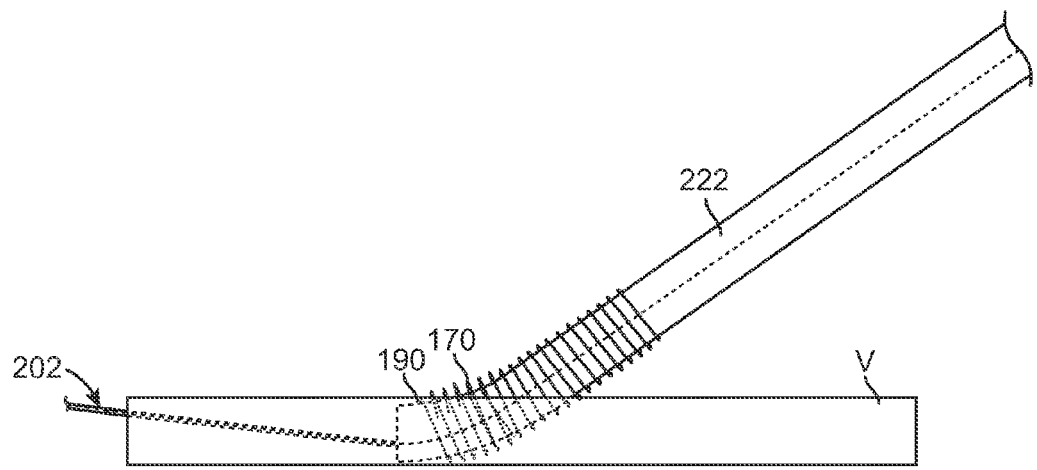

FIG. 17 shows the cutting or scoring dilator 210 being withdrawn, leaving the introducer sheath 222 in place through the tissue tract and into the lumen of the blood vessel V. The introducer sheath 222 also passes through the center of the helical coil of suture 170, as shown in FIG. 18.

Figure 19:
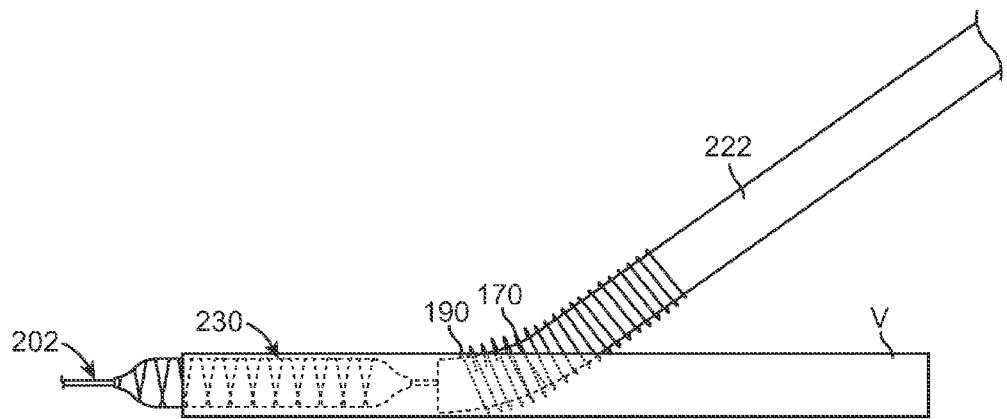

Once the introducer sheath 222 is in place, a variety of diagnostic, therapeutic and/or interventional devices 230 can be inserted through the introducer sheath 222, as shown in FIG. 19. The guidewire 202 may be used to introduce the interventional device 230 or it may be withdrawn and discarded if it is of no further use in the procedure. The interventional procedure may be performed anywhere in the vasculature that is accessible from the insertion site.

Figure 20:
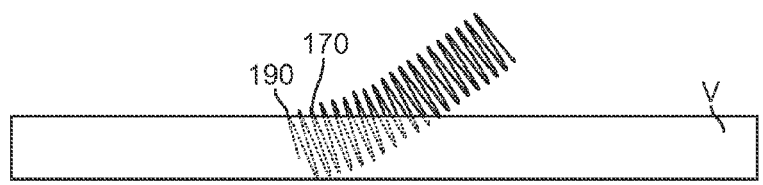
Figure 21:
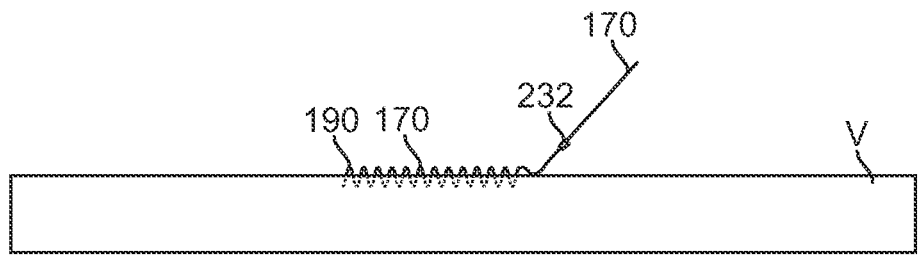
Figure 22:
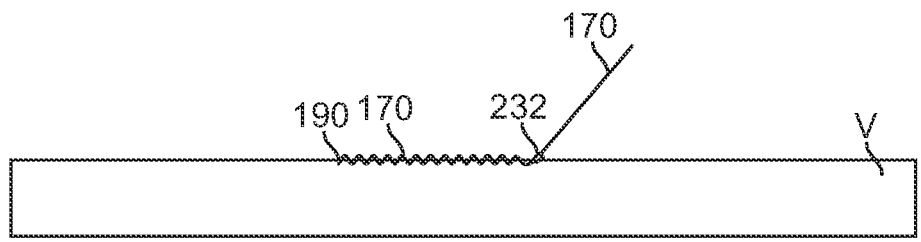

Once the interventional procedure has been completed, the interventional device 230 and then the introducer sheath 222 are withdrawn, leaving only the helical coil of suture 170 in place, as shown in FIG. 20. The suture 170 is pulled until it tightens from a loose coil into a running suture that closes the insertion site, as shown in FIG. 21. A knot or a suture lock 232 is placed on the suture 170 and slid down the suture 170 to lock the running suture in place, as shown in FIG. 22. A tube or a surgical knot pusher can be used to push the knot or suture lock 232 down through the tissue tract and along the suture 170. Optionally, the suture 170 may be cut off proximal to the suture lock 232. Optionally, an adhesive or sealant may be applied to the suture 170 and the insertion site. If necessary, additional sutures, adhesives or collagen plugs may be used to close and/or promote healing of the tissue tract.

A radiopaque contrast agent can be injected for confirmation of positioning and mapping of the blood vessel and its sidebranches by fluoroscopy at different points during the procedure. For example, the access needle 200, the guiding element 242, the vessel access and closure device 100, the dilator 210 and the introducer sheath 222 each have a lumen that can be used for radiopaque dye injections. In addition, each of the components may have radiopaque markers and/or be made of a radiopaque material to facilitate fluoroscopic imaging.

The following are given as nonlimiting examples of the dimensions and materials for some of the components of the vessel access and closure device 100. The helical suture needle 132 will preferably have a needle diameter in the range of approximately 0.015-0.050 inches, a helix diameter in the range of approximately 0.100-0.500 inches, and a length in the range of approximately 0.25-1.5 inches. The pitch or coil-to-coil distance of the helical suture needle 132 will preferably be in the range of approximately 0.030-0.125 inches and the number of coils or turns will be approximately 6-20. The elongated shaft portion 104 will preferably have an outside diameter in the range of approximately 0.100-0.375 inches and a length in the range of approximately 3-18 inches. The suture 170 will preferably be size 5-0 or larger and may be monofilament, braided, profiled shape (mono or braided), coated, dipped and/or lubricated and may be made from nylon, ultra high molecular weight polyethylene, silk, gut, expanded PTFE, absorbable polymers, etc. The guidewire will preferably have a diameter in the range of approximately 0.014-0.045 inches, more preferably 0.035-0.038 inches, though other sizes may also be used. The cutting or scoring dilator 210 will preferably have an outside diameter in the range of approximately 6-24 French (2-8 mm) and the introducer sheath 222 will preferably have an inside diameter in the range of approximately 6-24 French that is matched to the outside diameter of the cutting or scoring dilator 210.

Figure 23:
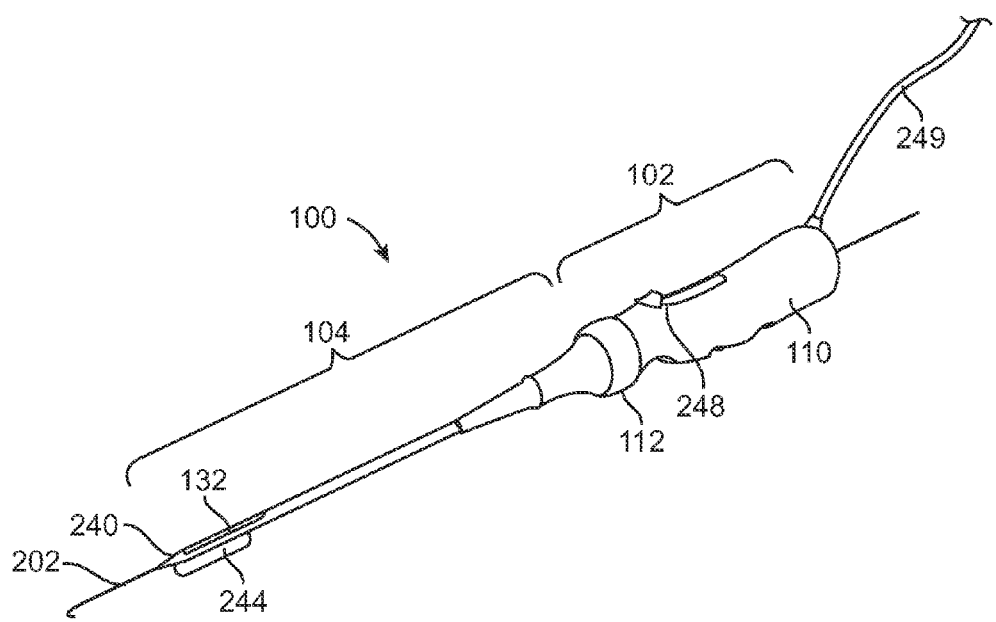
FIG. 23 is a perspective view and FIG. 24 is a front view illustrating another embodiment of the vessel access and closure device incorporating additional features.
Figure 24:
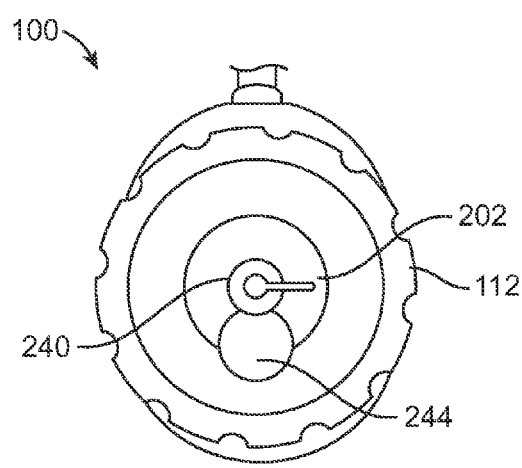

FIG. 23 is a perspective view and FIG. 24 is a front view illustrating another embodiment of the vessel access and closure device 100 incorporating some additional features. The vessel access and closure device 100 has an elongated shaft portion 104 connected to a proximal handle 102. In this embodiment, the rotating portion 112 is located on the distal end of the proximal handle 102, distal to the stationary portion 110. The rotating portion 112 is connected to the torque transmitting member 124 by a planetary gear mechanism or the like (not shown). A positioning device 240, similar to the one described above, is incorporated into the device 100. A sliding control button 248 on the proximal handle 102 controls the advancement and retraction of a retractable cutter that cuts a larger access opening at the puncture site. Optionally, the positioning device 240 may also be made retractable. Another sliding control button could be located on the proximal handle 102 to control the advancement and retraction of the positioning device 240. An inflation tube with a stopcock 249 connects to a pressure source, such as a syringe (not shown), for inflating and deflating the balloon 244. Because the positioning device 240 is connected to the proximal handle 102, the correct orientation of the balloon 244 in the blood vessel is assured.

In other embodiments of the vessel access and closure device 100, a motor or other mechanism may be provided to drive the rotation of the helical suture needle 132. The motor may be located in the proximal or distal end of the device 100. Other manually operated mechanisms may also be used to drive the rotation of the helical suture needle 132. For example, a handle or trigger may be connected to the torque transmitting member 124 by a rack-and-pinion or other gear mechanism that turns linear motion to rotary. The handle or trigger would be squeezed to rotate the helical suture needle 132. A lever or knob may be provided to reverse the direction of rotation.

Figure 25:
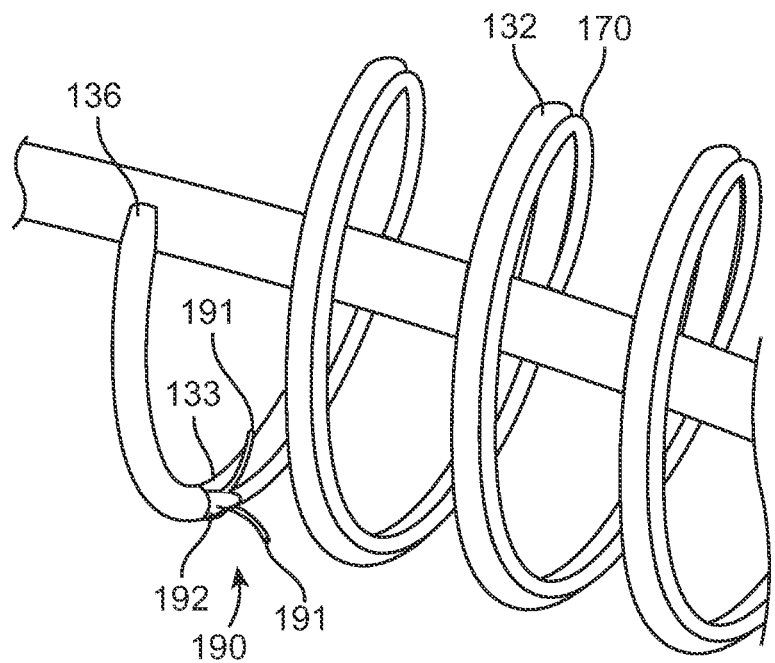
FIG. 25 shows an enlarged view of the helical suture needle with the suture and the suture anchor.

FIG. 25 shows an enlarged view of the helical suture needle 132 with the suture 170 and the suture anchor 190. The suture anchor 190 is attached to the distal end of the suture 170, for example by adhesive, overmolding, crimping, swaging, tying or forming integrally with it. The suture anchor 190 is releasably attached to the helical suture needle 132 by a ring or collar 192 that fits around the suture needle 132 and rests against a shelf or ledge 133 on the suture needle 132. The suture anchor 190 has at least one, and preferably two or more, resilient barbs 191 that are angled backward so the suture anchor 190 will move easily through the tissue in a forward direction along with the helical suture needle 132. When the direction of the helical suture needle 132 is reversed, the barbs 191 will spread to anchor the suture anchor 190 and the suture 170 to the blood vessel wall. The reverse motion will also dislodge the collar 192 of the suture anchor 190 from the shelf or ledge 133, thus releasing the suture anchor 190 from the suture needle 132.

Figure 26:
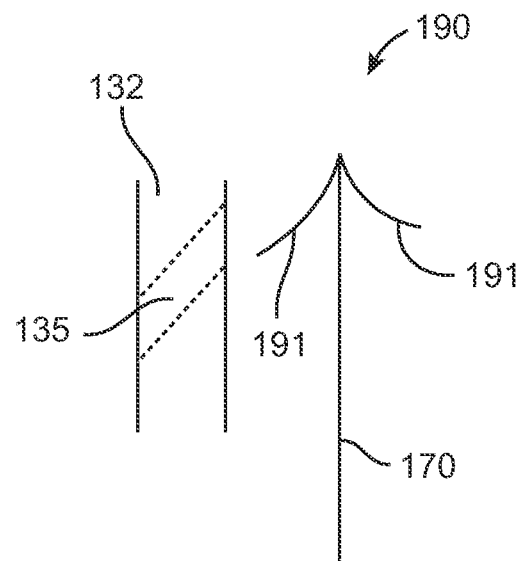
FIG. 26 shows an enlarged view of another variation of the suture anchor.

FIG. 26 shows an enlarged view of another variation of the suture anchor 190. The suture anchor 190 is attached to the distal end of the suture 170, for example by adhesive, overmolding, crimping, swaging, tying or forming integrally with it. As above, the suture anchor 190 has a pair of resilient barbs 191 that are angled backward. In this variation, the suture anchor 190 is releasably attached to the helical suture needle 132 by inserting one of the barbs 191 into an obliquely drilled hole 135 in the suture needle 132. The backward-angled resilient barb 191 allows the suture anchor 190 to move easily through the tissue in a forward direction along with the helical suture needle 132. When the direction of the helical suture needle 132 is reversed, the barbs 191 will spread to anchor the suture anchor 190 and the suture 170 to the blood vessel wall. The reverse motion will also dislodge the suture anchor 190 from the hole 135, thus releasing the suture anchor 190 from the suture needle 132.

Figure 27:
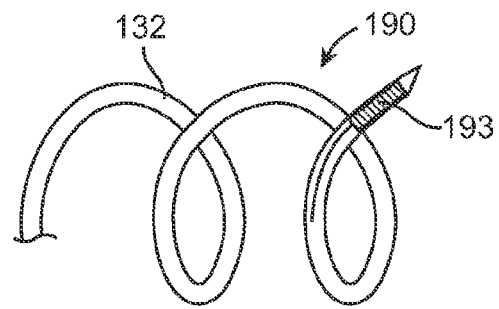
FIGS. 27 and 28 illustrate a helical suture needle with a toggle-shaped suture anchor.
Figure 28:
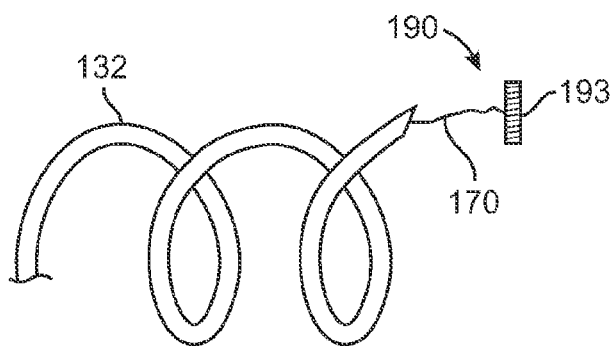

As mentioned previously, the helical suture needle 132 may be tubular, formed for example from stainless steel or NiTi alloy hypodermic needle tubing. The suture 170 and the suture anchor 190 may fit inside of the helical suture needle 132, as shown in FIG. 27. The suture anchor 190 may have barbs, as described above, or it may be configured as a simple toggle 193 attached near its middle to the suture 170. After the helical suture needle 132 has advanced through the blood vessel wall, the toggle 193 is ejected from the helical suture needle 132, preferably on the exterior of the blood vessel, to anchor the suture 170, as shown in FIG. 28.

Figure 29:
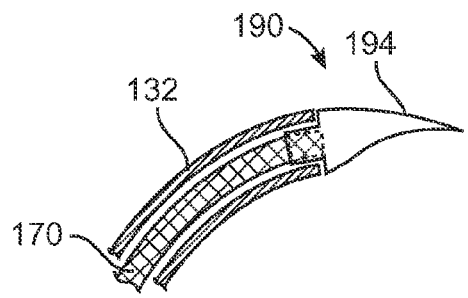
FIG. 29 shows a suture anchor with a tissue-piercing point configured to fit into the tubular distal end of a helical suture needle.

FIG. 29 shows a suture anchor 190 with a tissue-piercing point 194 that is configured to fit into the tubular distal end of a helical suture needle 132. The suture anchor 190 may have barbs, as described above, or it may be attached to the suture 170 near its middle to act as a toggle fastener.

Figure 30:
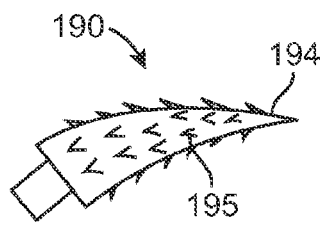
FIG. 30 shows another suture anchor with a tissue-piercing point configured with a multiplicity of small barbs.

FIG. 30 shows another suture anchor 190 with a tissue-piercing point 194 that is configured with a multiplicity of small barbs 195 to anchor the suture 170 to the blood vessel wall or surrounding tissue.

The suture anchors 190 shown in FIGS. 29 and 30 can also be adapted fit onto the distal end of a solid helical suture needle 132.

FIGS. 31 and 32 show a distal portion of a tubular helical suture needle 132 with a suture anchor 190 made of a superelastic or shape memory NiTi alloy wire 196. A distal portion of the wire 196 is preformed by heat treating into a curvature, for example a spiral coil, that will act as a suture anchor 190, as shown in FIG. 32. The curvature in the wire 196 can be straightened out by drawing it into tubular helical suture needle 132, as shown in FIG. 31. After the helical suture needle 132 has advanced through the blood vessel wall, the wire 196 is advanced out of the helical suture needle 132, preferably on the exterior of the blood vessel, and the curvature reforms to anchor the suture 170, as shown in FIG. 32.

FIGS. 33, 34 and 35 show a distal portion of a tubular helical suture needle 132 with a suture anchor 190 configured as an expandable cage 197, preferably of superelastic or shape memory NiTi alloy wire. The expandable cage 197 can be compressed to fit into the tubular helical suture needle 132, as shown in FIG. 33. After the helical suture needle 132 has advanced through the blood vessel wall, the expandable cage 197 is ejected from the helical suture needle 132, preferably on the exterior of the blood vessel, and the expandable cage 197 expands to anchor the suture 170, as shown in FIG. 34. FIG. 35 shows the expandable cage 197 of the suture anchor 190 anchoring the suture 170 to the wall of the blood vessel V.

The following describes additional features of the invention that may be combined with the embodiments of the vessel access and closure device 100 described above.

Optionally, excitation of the helical suture needle 132 with subsonic, sonic or ultrasonic vibration may be used to facilitate passing the needle through the wall of the blood vessel. This feature may be especially advantageous when the walls of the blood vessel are heavily calcified. Another way to facilitate passing the needle through the wall of the blood vessel would be to wind up and release stored spring energy in the helical suture needle 132 to move the distal tip 136 of the needle forward quickly to pierce the vessel wall.

Similarly, excitation of the cutting or scoring dilator 210 and/or the cutting or scoring element 214 with subsonic, sonic or ultrasonic vibration may be used to facilitate cutting and dilating the access opening through the wall of the blood vessel.

Figure 36A:
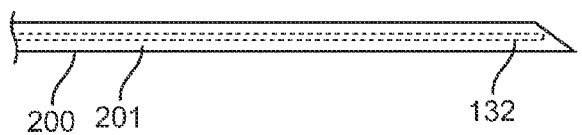
FIGS. 36A-36B illustrate a helical suture needle made from a superelastic NiTi alloy.
Figure 37A:
FIGS. 37A-37D illustrate a guiding element with a D-shaped cross section.
Figure 36B:
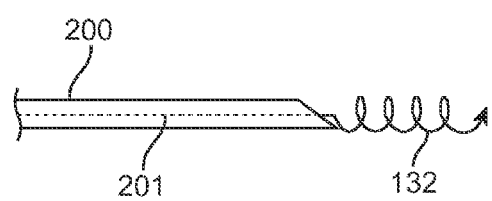

FIGS. 36A-36B illustrate a helical suture needle 132 made from a superelastic NiTi alloy. The helical suture needle 132 can be straightened out for insertion though a small diameter lumen 201 in an access needle 200 or other device, as shown in FIG. 36A. Once the superelastic helical suture needle 132 is out of the lumen 201, it resumes its helical configuration, as shown in FIG. 36B.

Figure 37B:
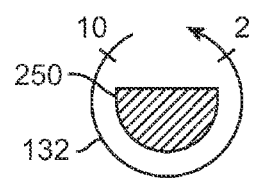
Figure 37C:
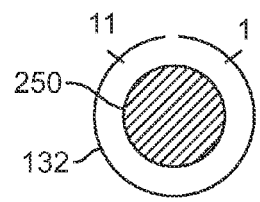
Figure 37D:
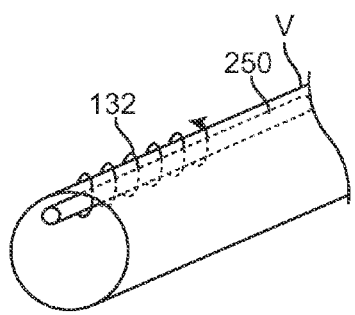

FIGS. 37A-37D illustrate another embodiment of a guiding element 250 with a D-shaped cross section. The guiding element 250 with a D-shaped cross section can be a separate device or it can be incorporated into either the guidewire 202 and/or the positioning device 240 described above. Optionally, the D-shaped guiding element 250 may have a guidewire lumen so that it can be introduced over the guidewire 202. With the D-shaped guiding element 250 pressed against the inside of the blood vessel wall, as shown in FIG. 37B, the helical suture needle 132 will be constrained to pass through the blood vessel wall at the 10 o'clock and 2 o'clock positions. FIG. 37C shows how, with a change in the geometry of the D-shaped guiding element 250, the helical suture needle 132 can be made to pass through the blood vessel wall at the 11 o'clock and 1 o'clock positions, or any desired positions. FIG. 37D is a perspective view of the D-shaped guiding element 250 pressed against the inside of the blood vessel V with the helical suture needle 132 rotating around it to place a running suture in the blood vessel wall.

Figure 38:
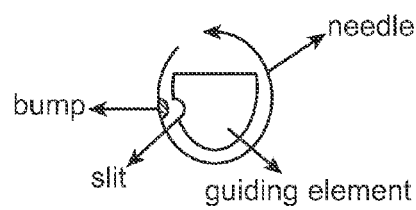
FIG. 38 illustrates a D-shaped guiding element with additional feature.

As shown in FIG. 38, the D-shaped guiding element 250 may also be configured with a longitudinal groove 251 that interacts with a bump 137 on the helical suture needle 132 to make click that provides a tactile indication to the operator every time the helical suture needle 132 makes a revolution.

Figure 39:
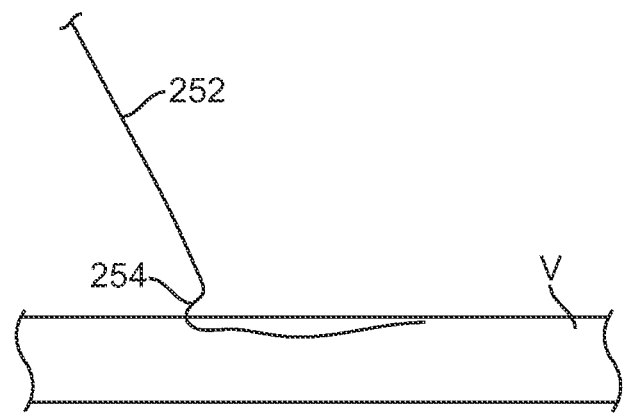
FIG. 39 shows another embodiment of a guiding element having a back turn.

FIG. 39 shows another embodiment of a guiding element 252 with a back turn 254. The guiding element 252 may have a round, elliptical or D-shaped cross section, as described above. The back turn 254 guides the helical suture needle 132 so that it will place one or more stitches in the vessel wall proximal to the puncture site.

Figure 40:
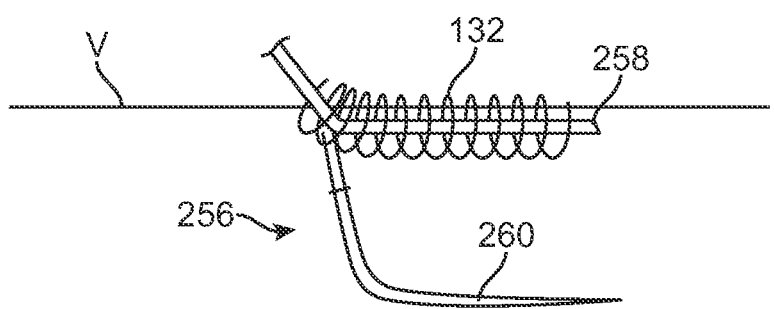
FIG. 40 shows a spacer mechanism that presses the guiding element against the near wall of the blood vessel.

FIG. 40 shows a spacer mechanism 256 that assures that the guiding element 258 will be pressed against the near wall of the blood vessel V. The spacer mechanism 256 has a second arm 260 that presses against the far wall of the blood vessel V, forcing the guiding element 258 against the near wall of the blood vessel V. The spreading force between the second arm 260 and the guiding element 258 can be from spring action, for example the second arm 260 can be made of a spring material (e.g. stainless steel or a NiTi alloy). Alternatively, the spreading force can be applied from the proximal ends of the second arm 260 and the guiding element 258, manually, with a spring or with an inflatable member.

Figure 41:
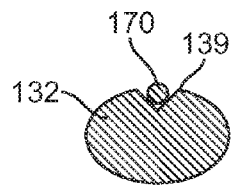
FIG. 41 shows a cross section of a helical suture needle with a V-shaped groove for holding a suture.
Figure 42:
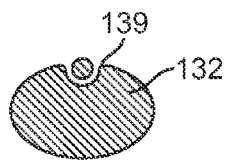
FIG. 42 shows a cross section of a helical suture needle with a U-shaped groove for holding a suture.
Figure 43:
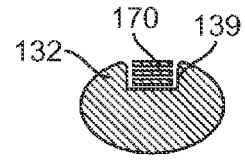
FIG. 43 shows a cross section of a helical suture needle with a rectangular channel for holding a suture.

In one option, the suture 170 will be carried on the exterior of the helical suture needle 132 with a channel or groove 139 to carry the suture 170. FIG. 41 shows one alternative for the cross section of the helical suture needle 132. The suture needle 132 is generally round with a V-shaped groove 139 for holding a round suture 170. FIG. 42 shows another alternative for the cross section of the helical suture needle 132. The suture needle 132 is generally round with a U-shaped groove 139 for holding a round suture 170. FIG. 43 shows another alternative for the cross section of the helical suture needle 132. The suture needle 132 is generally round with a rectangular channel 139 for holding a round or flat suture 170. The channel or groove 139 may be oriented in any direction on the suture needle 132 with respect to the axis of the helix.

Figure 44:
FIG. 44 illustrates a flat suture that is folded back on itself for storing additional length of suture.

It may be advantageous to have additional length of suture 170 carried on the helical suture needle 132 so that the helical coil of suture 170 placed in the vessel wall can open up to a larger diameter to accommodate a large diameter introducer sheath and/or interventional device. FIGS. 43 and 44 illustrate one option for storing additional length of suture 170 on the helical suture needle 132. As shown in FIG. 44, a flat suture 170 can be folded back on itself at regular and periodic intervals along the suture 170. Optionally, the suture 170 may be tacked with an adhesive 171 to keep it in the folded configuration during insertion of the helical suture needle 132. FIG. 43 shows how the flat suture 170 can lay stacked in a rectangular channel 139 on the helical suture needle 132. An amount of suture 170 up to three times the length of the helical suture needle 132 can be stored in the channel 139. After the suture 170 has been placed in the vessel wall, the helical coil of suture 170 can be enlarged using a tapered dilator or inflatable balloon.

Figure 45:
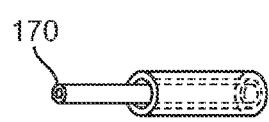
FIGS. 45, 46 and 47 illustrate how a tubular suture can be prolapsed onto itself to store additional length of suture.
Figure 46:
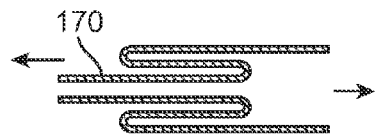
Figure 47:

FIGS. 45, 46 and 47 show how a tubular suture 170 can be prolapsed onto itself to store additional length of suture 170 on the helical suture needle 132 analogously to the folded flat suture described above. This option may be particularly applicable to tubular braided sutures. FIG. 45 is a perspective view and FIG. 46 is a longitudinal cross section of the tubular suture 170 in a prolapsed position. FIG. 47 shows the tubular suture 170 drawn out to its full length. Alternatively, tubular braided sutures can be compressed axially without prolapsing. The diameter of a tubular braid increases as its length decreases by axial compression.

Figure 48:
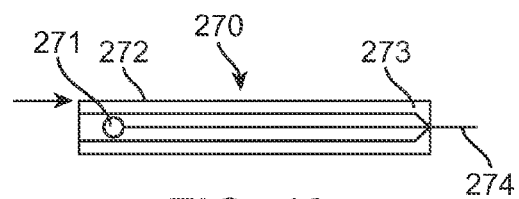
FIGS. 48 and 49 illustrate a telescopically expandable suture.
Figure 49:
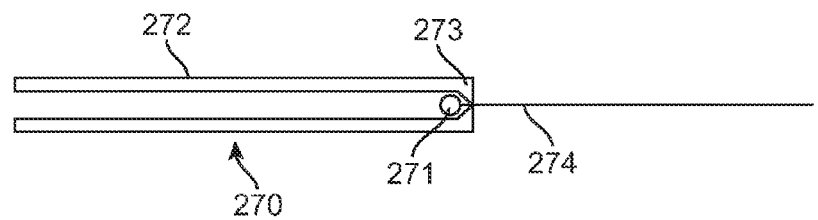

FIGS. 48 and 49 show a telescopically expandable suture 270 that has a tubular portion 272 surrounding a small diameter portion 274. FIG. 48 shows the telescopically expandable suture 270 in a retracted position. FIG. 49 shows the telescopically expandable suture 270 in an extended position. A knot or bead 271 on the small diameter portion 274 stops at a reduced diameter area 273 on the end of the tubular portion 272 to limit the telescopic elongation of the suture 270. Optionally, the telescopically expandable suture 270 may have several repeating units of tubular portions 272 surrounding small diameter portions 274.

Another option would be to make the suture 170, 270 from a material that can be elastically or plastically elongated. The suture 170, 270 could then be stretched to enlarge the helical coil of suture after it has been stitched in place through the blood vessel wall.

Another option would be to provide additional suture length by storing the suture 170 in a helically coiled or zigzag pattern on the interior or the exterior of the helical suture needle 132.

Figures 50, 51:
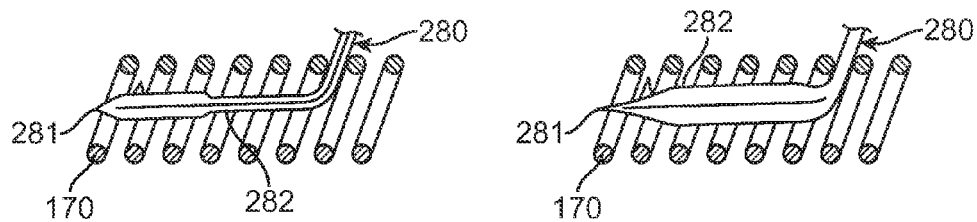
FIGS. 50 and 51 illustrate an expanding dilator.

FIGS. 50 and 51 show an expanding dilator 280 that may be used with the vessel access and closure device 100. The expanding dilator 280 has a tapered distal end 281 and a dilator body 282 with a small-diameter profile that facilitates its entry through the blood vessel wall and into the helical coil of suture 170, as shown in FIG. 50. After the expanding dilator 280 is in place, the dilator body 282 can be expanded, for example by inflation with a fluid, to widen the puncture site in the vessel wall and/or to expand the helical coil of suture 170, as shown in FIG. 51. The tapered distal end 281 and/or the dilator body 282 may optionally include a cutting or scoring element, as described above.

Figure 52:
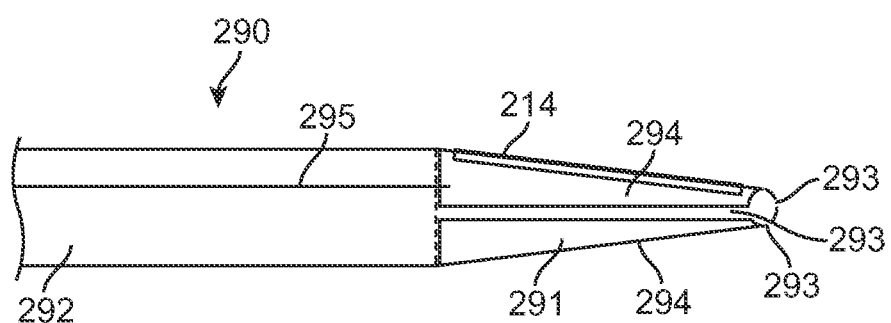
FIGS. 52 and 53 illustrate a dilator with an expandable tapered tip.
Figure 53:
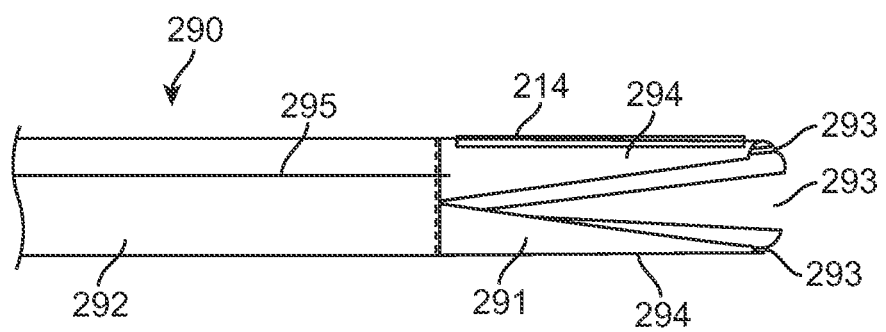

Another option for the vessel access and closure device 100 is a dilator 290 with an expandable tapered tip 291. The expandable tapered tip 291 is attached to a cylindrical dilator body 292 and has a plurality of slits 293 that divide the tapered tip 291 into an equal number of sectors 294. In the example shown, the expandable tapered tip 291 has four slits 293 that divide the tapered tip 291 into four sectors 294. In a closed position, the expandable tapered tip 291 is approximately conical, as shown in FIG. 52. Optionally, the expandable tapered tip 291 may have a cutting or scoring element 214 located on one of the sectors 294, preferably located at a 12 o'clock position. The expandable tapered tip 291 has an open position where the sectors 294 spread out to the same diameter as the cylindrical dilator body 292 or even larger if desired, as shown in FIG. 53. The expandable tip dilator 290 can be used as a normal tapered dilator or the expanding action of the tip 291 can optionally be used to dilate the puncture site in the blood vessel wall and/or to dilate the helical coil of suture 170 to a larger diameter. Once the dilator 290 is in place in the lumen of the blood vessel, the expandable tapered tip 291 can be opened up so that the cylindrical dilator body 292 can be used as an introducer sheath. A pull wire 295 or other mechanism in the dilator 290 may be used to expand the tapered tip 291. Examples of other mechanisms that could be used to open the expandable tapered tip 291 include internal pressure created by insertion of an interventional device or catheter, inflation of a balloon inserted through or integrated into the dilator 290, a small motor, push wires, drive shaft, magnetic force, hydraulic force, electro active polymers, a shape memory NiTi alloy, etc. Optionally, the cutting or scoring element 214 may be retractable to avoid the risk of cutting the suture 170 when the expandable tapered tip 291 is in the open position. Another option would be to configure the vessel dilator with a removable tapered tip that can be withdrawn once the dilator is in the lumen of the blood vessel, allowing the cylindrical dilator body to be used as an introducer sheath.

Another option is a vessel dilator with a screw-shaped tapered tip that can be rotated to gradually and controllably dilate the puncture site through the vessel wall.

Figure 54:
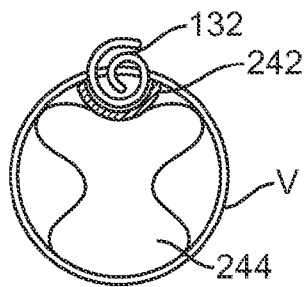
FIG. 54 illustrates an inflatable balloon with a nonoccluding figure eight or hourglass cross section.
Figure 55:
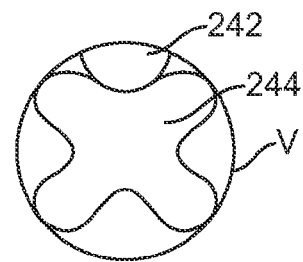
FIG. 55 illustrates an inflatable balloon with a nonoccluding X-shaped cross section.

Optionally, the inflatable balloon 244 that serves as a biasing element for the guiding element 242 described above may be configured with a noncircular cross section in order to avoid occluding blood flow through the vessel lumen to the extremities or other organs downstream. FIG. 54 illustrates an inflatable balloon 244 with a nonoccluding figure eight or hourglass cross section. FIG. 55 illustrates an inflatable balloon 244 with a nonoccluding X-shaped cross section.

Figure 56:
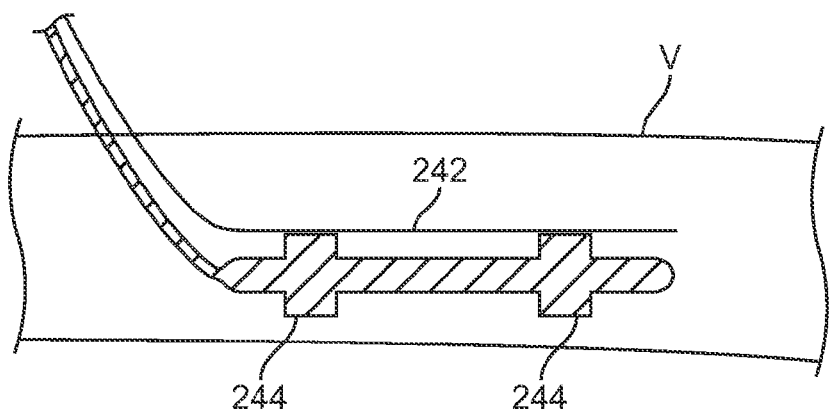
FIGS. 56 and 57 illustrate an inflatable balloon in a barbell configuration.
Figure 57:
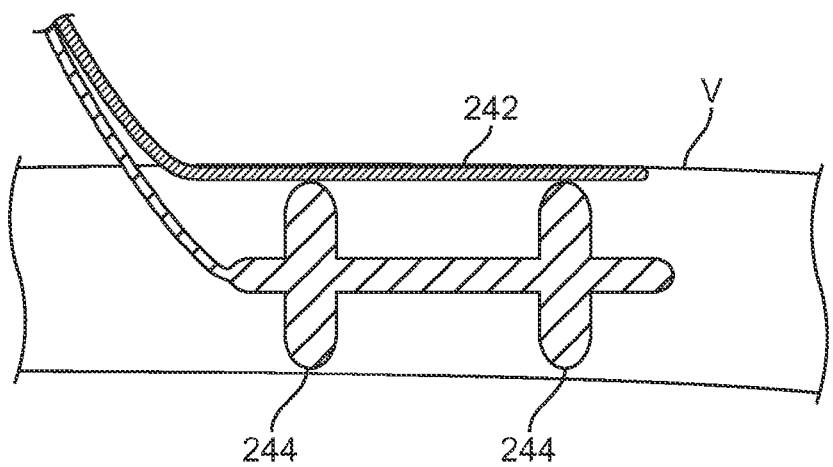

FIGS. 56 and 57 show another optional configuration for an inflatable balloon 244 for use as a biasing element for the guiding element 242. The inflatable balloon 244 is in a barbell configuration, either with a pair of inflatable portions or one single barbell-shaped balloon. When the balloon 244 is inflated, the guiding element 242 is positioned against the near wall of the blood vessel.

As mentioned above, it is most desirable to place the suture anchor 190 on the exterior of the blood vessel wall in order to avoid the suture anchor 190 from becoming a nidus for thrombus formation or other complications. In addition to the position indicating mechanisms described above, it may be desirable to provide for sensing the position of the needle tip 136 and/or the suture anchor 190. One method of sensing the position of the needle tip 136 is with conduction. If all of the helical suture needle 132 except for the distal tip 136 is covered with an insulative coating, a conductivity or impedance sensor in contact with the blood in the vessel lumen will be able to determine when the needle tip 136 is inside or outside of the vessel lumen. Another method would be to place a magnetic element on the distal tip 136 of the helical suture needle 132 and to use a magnetic sensor or imaging device to detect the position and the orientation of the magnetic poles.

Figure 58:
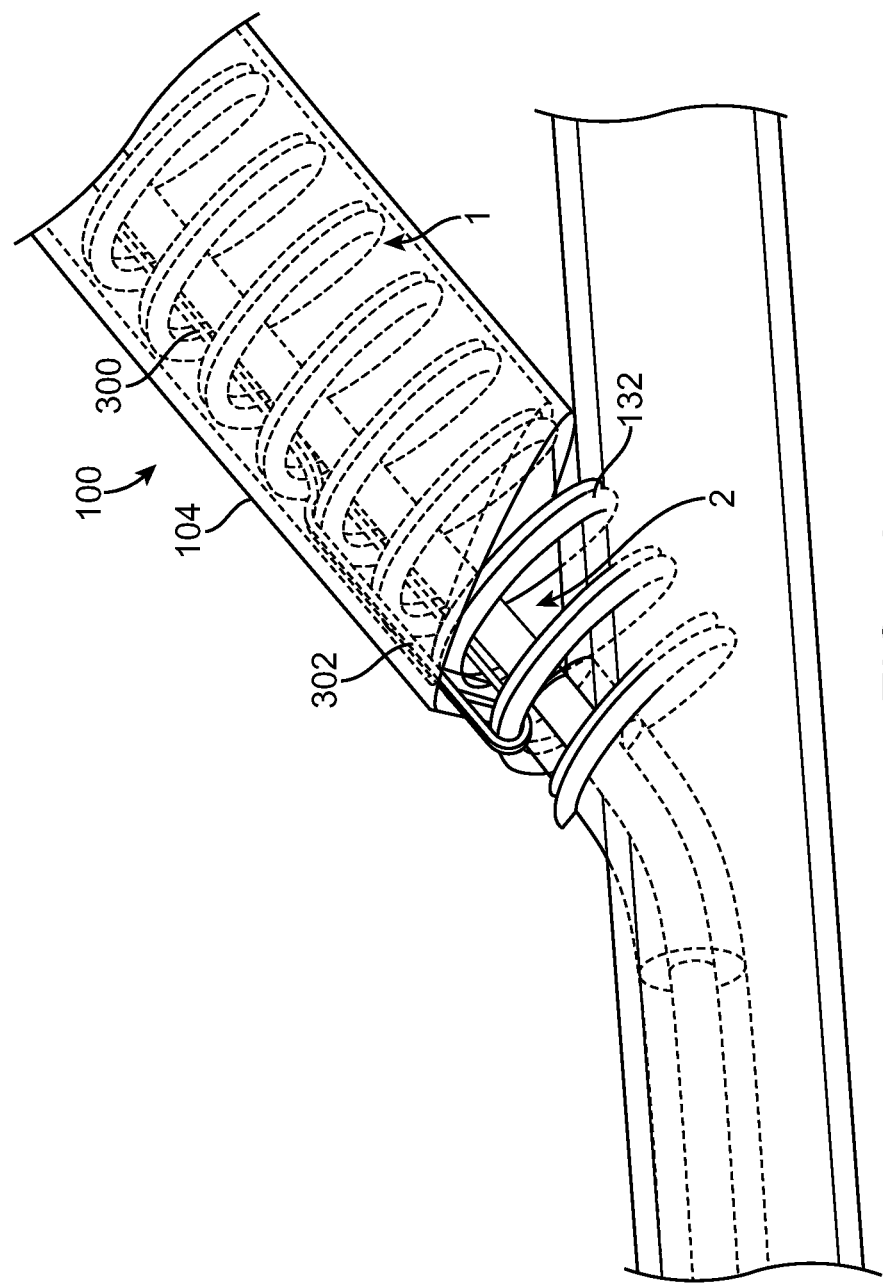
FIG. 58 illustrates a coil buncher device for deflecting or redirecting the helical surgical needle.

FIG. 58 shows an alternative method for redirecting the helical surgical needle 132. A coil buncher device 300 extends through the elongated shaft portion 104 of the vessel access and closure device 100 and a loop 302 on the distal end of the coil buncher device 300 bunches up the coils of the helical surgical needle 132 on one side, deflecting or redirecting the helical surgical needle 132. Optionally, the coil buncher device 300 can be made adjustable so that the angle of deflection of the helical surgical needle 132 can be varied. The coil buncher device 300 can also be rotated within the vessel access and closure device 100 to change the direction of the helical surgical needle 132 from longitudinal to oblique, to perpendicular to the longitudinal axis of the blood vessel.

Although a longitudinal opening and suture line are thought to be preferred for vessel access and closure at this time, the vessel access and closure device of the present invention can also be adapted to create and subsequently close an opening at any angle on the vessel wall. For example, the opening and the suture line could be transverse or diagonal, for example at a 45 degree angle to the longitudinal axis of the blood vessel. Optionally, a helically-shaped guiding element that follows the inner surface of the blood vessel wall could be used to guide the helical suture needle 132 along a diagonal path.

The vessel access and closure device described herein could also be used to close other tubular organs (intestine, esophagus, airways, etc.) and also non tubular organs (abdominal fascia, etc.)

While the present invention has been described herein with respect to the exemplary embodiments and the best mode for practicing the invention, it will be apparent to one of ordinary skill in the art that many modifications, improvements, combinations and subcombinations of the various features and embodiments, adaptations and variations can be made to the invention without departing from the spirit and scope thereof.

What is claimed is:

1. A blood vessel access and closure device, comprising:
   a helical suture needle having a proximal end and a distal end;
   a torque transmitting member having a proximal end and a distal end, the distal end of the torque transmitting member being attached to the proximal end of the helical suture needle;
   a suture having a proximal end and a distal end, the distal end of the suture being releasably attached near the distal end of the helical suture needle;
   a suture anchor attached to the distal end of the helical suture;
   a vessel dilator having a proximal end and a distal end, the vessel dilator having a tapered distal portion connected to a cylindrical body; and
   a cutting element located on the tapered distal portion of the vessel dilator.

2. The blood vessel access and closure device of claim 1, wherein the torque transmitting member is a torque tube having a central lumen extending therethrough.

3. The blood vessel access and closure device of claim 1, further comprising:
an outer tube surrounding the torque transmitting member.

4. The blood vessel access and closure device of claim 3, further comprising:
a suturing tip connected to a distal end of the outer tube, the suturing tip being configured to redirect the helical suture needle from an orientation aligned with a longitudinal axis of the outer tube to an orientation aligned with a second axis that is at an angle with respect to the longitudinal axis of the outer tube.

5. The blood vessel access and closure device of claim 4, further comprising:
a needle guide located within the outer tube proximal to the suturing tip, the needle guide having a helical groove configured to engage the helical suture needle.

6. The blood vessel access and closure device of claim 3, further comprising:
a stationary handle attached to a proximal end of the outer tube; and
a rotatable handle attached to a proximal end of the torque transmitting member.

7. The blood vessel access and closure device of claim 6, wherein the stationary handle and the rotatable handle are configured to limit axial movement of the torque transmitting member with respect to the outer tube.

8. The blood vessel access and closure device of claim 1, further comprising:
an introducer sheath having a sheath lumen that is positioned around the cylindrical body of the vessel dilator.

9. The blood vessel access and closure device of claim 1, further comprising:
a scoring element located on the tapered distal portion of the vessel dilator.

10. The blood vessel access and closure device of claim 1, wherein the helical suture needle is tubular with a needle lumen extending therethrough, and the suture extends through the needle lumen.

11. The blood vessel access and closure device of claim 1, wherein the helical suture needle has a suture channel extending along an exterior of the helical suture needle, and the suture extends through the suture channel.

12. The blood vessel access and closure device of claim 1, wherein the distal end of the suture is releasably attached near the distal end of the helical suture needle by the suture anchor.

13. The blood vessel access and closure device of claim 1, wherein the suture anchor has at least one barb for attaching the suture anchor to a wall of a blood vessel.

14. The blood vessel access and closure device of claim 1, wherein the suture anchor has a retracted position and an expanded position, wherein, in the expanded position, the suture anchor is configured for attaching the suture anchor to a wall of a blood vessel.

15. The blood vessel access and closure device of claim 1, wherein the suture anchor is releasably attached to the distal end of the helical suture needle, and the suture anchor has a sharpened distal tip for penetrating a wall of a blood vessel.

16. The blood vessel access and closure device of claim 1, wherein the distal end of the helical suture needle has a sharpened distal tip for penetrating a wall of a blood vessel.

17. The blood vessel access and closure device of claim 1, further comprising:
a positioning device having an elongated guiding member and an eccentrically expandable biasing member mounted near a distal end of the elongated guiding member.

18. The blood vessel access and closure device of claim 17, wherein the eccentrically expandable biasing member is an inflatable balloon mounted on one side of the elongated guiding member.

19. The blood vessel access and closure device of claim 17, wherein the eccentrically expandable biasing member comprises a spacer arm that is biased to move away from the elongated guiding member.

20. The blood vessel access and closure device of claim 1, further comprising:
a hemostasis valve configured to allow insertion of a guidewire through the blood vessel access and closure device while controlling bleeding through the blood vessel access and closure device.

21. The blood vessel access and closure device of claim 1, further comprising:
a guiding element having a D-shaped cross section configured to guide the helical suture needle on a path through a wall of a blood vessel.

22. A blood vessel access and closure device, comprising:
a helical suture needle having a proximal end and a distal end;
a torque transmitting tube having a proximal end and a distal end, the distal end of the torque transmitting tube being attached to the proximal end of the helical suture needle;
an outer tube surrounding the torque transmitting tube;
a stationary handle attached to a proximal end of the outer tube;
a rotatable handle attached to a proximal end of the torque transmitting member, wherein the stationary handle and the rotatable handle are configured to limit axial movement of the torque transmitting tube with respect to the outer tube;
a suturing tip connected to a distal end of the outer tube, the suturing tip being configured to redirect the helical suture needle from an orientation aligned with a longitudinal axis of the outer tube to an orientation aligned with an axis that is at an angle with respect to the longitudinal axis of the outer tube;
a needle guide located within the outer tube proximal to the suturing tip, the needle guide having a helical groove configured to engage the helical suture needle;
a suture having a proximal end and a distal end;
a suture anchor attached to the distal end of the helical suture, the suture anchor being releasably attached near the distal end of the helical suture needle;
a vessel dilator having a proximal end and a distal end, the vessel dilator having a tapered distal portion connected to a cylindrical body;
a cutting or scoring element located on the tapered distal portion of the vessel dilator; and
an introducer sheath having a sheath lumen that is positioned around the cylindrical body of the vessel dilator.

23. A system for blood vessel access and closure, comprising:
an access needle having a needle lumen extending therethrough;
a guidewire insertable through the needle lumen of the access needle, the guidewire having a distal portion and a proximal portion with a bend between the distal portion and the proximal portion;
a blood vessel access and closure device, comprising:

a helical suture needle having a proximal end and a distal end;

a torque transmitting member having a proximal end and a distal end, the distal end of the torque transmitting member being attached to the proximal end of the helical suture needle;

a suture having a proximal end and a distal end, the distal end of the suture being releasably attached near the distal end of the helical suture needle;

a suture anchor attached to the distal end of the helical suture;

a vessel dilator having a proximal end and a distal end, the vessel dilator having a tapered distal portion connected to a cylindrical body;

a cutting element located on the tapered distal portion of the vessel dilator; and an introducer sheath having a sheath lumen that is positioned around the cylindrical body of the vessel dilator.

24. The system of claim 23, wherein the torque transmitting member is a torque tube having a central lumen extending therethrough.

25. The system of claim 23, further comprising:
an outer tube surrounding the torque transmitting member.

26. The system of claim 25, further comprising:
a suturing tip connected to a distal end of the outer tube, the suturing tip being configured to redirect the helical suture needle from an orientation aligned with a longitudinal axis of the outer tube to an orientation aligned with a second axis that is at an angle with respect to the longitudinal axis of the outer tube.

27. The system of claim 26, further comprising:
a needle guide located within the outer tube proximal to the suturing tip, the needle guide having a helical groove configured to engage the helical suture needle.

28. The system of claim 23, further comprising:
a scoring element located on the tapered distal portion of the vessel dilator.

29. The system of claim 25, further comprising:
a stationary handle attached to a proximal end of the outer tube; and
a rotatable handle attached to a proximal end of the torque transmitting member.

30. The system of claim 23, wherein the helical suture needle is tubular with a needle lumen extending therethrough, and the suture extends through the needle lumen.

31. The system of claim 23, wherein the helical suture needle has a suture channel extending along an exterior of the helical suture needle, and the suture extends through the suture channel.

32. The system of claim 23, wherein the distal end of the suture is releasably attached near the distal end of the helical suture needle by the suture anchor.

33. The system of claim 23, wherein the suture anchor has at least one barb for attaching the suture anchor to a wall of a blood vessel.

34. The system of claim 23, wherein the suture anchor has a retracted position and an expanded position, wherein, in the expanded position, the suture anchor is configured for attaching the suture anchor to a wall of a blood vessel.

35. The system of claim 23, wherein the suture anchor is releasably attached to the distal end of the helical suture needle, and the suture anchor has a sharpened distal tip for penetrating a wall of a blood vessel.

36. The system of claim 23, wherein the distal end of the helical suture needle has a sharpened distal tip for penetrating a wall of a blood vessel.

37. The system of claim 23, further comprising:
a positioning device having an elongated guiding member and an eccentrically expandable biasing member mounted near a distal end of the elongated guiding member.

38. The system of claim 37, wherein the eccentrically expandable biasing member is an inflatable balloon mounted on one side of the elongated guiding member.

39. The system of claim 37, wherein the eccentrically expandable biasing member comprises a spacer arm that is biased to move away from the elongated guiding member.

40. The system of claim 23, further comprising:
a hemostasis valve configured to allow insertion of the guidewire through the blood vessel access and closure device while controlling bleeding through the blood vessel access and closure device.

41. The system of claim 23, further comprising:
a guiding element having a D-shaped cross section configured to guide the helical suture needle on a path through a wall of a blood vessel.

* * * * *